(12) United States Patent
Zhang et al.

(10) Patent No.: US 7,786,134 B2
(45) Date of Patent: Aug. 31, 2010

(54) LIPOPHILIC ANTICANCER DRUG COMPOUNDS, COMPOSITIONS AND RELATED METHODS

(75) Inventors: Yuehua Zhang, Bothell, WA (US); Lynn C. Gold, Seattle, WA (US)

(73) Assignee: Sonus Pharmaceuticals, Inc., Bothell, WA (US)

( * ) Notice: Subject to any disclaimer, the term of this patent is extended or adjusted under 35 U.S.C. 154(b) by 928 days.

(21) Appl. No.: 11/611,457

(22) Filed: Dec. 15, 2006

(65) Prior Publication Data

US 2007/0142331 A1 Jun. 21, 2007

Related U.S. Application Data

(60) Provisional application No. 60/751,219, filed on Dec. 16, 2005, provisional application No. 60/753,967, filed on Dec. 23, 2005.

(51) Int. Cl.
*A61K 31/4745* (2006.01)
*C07D 491/22* (2006.01)

(52) U.S. Cl. .................................. 514/283; 546/48

(58) Field of Classification Search ............... 514/283; 546/48

See application file for complete search history.

(56) References Cited

U.S. PATENT DOCUMENTS

| 6,291,676 | B1 | 9/2001 | Burke | |
|---|---|---|---|---|
| 7,223,770 | B2 * | 5/2007 | Zhang et al. | ............. 514/283 |
| 2004/0258754 | A1 | 12/2004 | Alakhov | |

FOREIGN PATENT DOCUMENTS

| EP | 0321122 A2 | 6/1989 |
|---|---|---|
| GB | 2056973 A | 3/1981 |
| WO | WO 9639143 A1 | 12/1996 |
| WO | WO 9835940 A1 | 8/1998 |
| WO | WO 03095460 A1 | 11/2003 |

* cited by examiner

*Primary Examiner*—Charanjit S Aulakh
(74) *Attorney, Agent, or Firm*—Christensen O'Connor Johnson Kindness PLLC

(57) ABSTRACT

Lipophilic anticancer drug compounds, compositions that include the compounds, and methods for treating a cell proliferative disease using the compounds.

16 Claims, 17 Drawing Sheets

LIPOPHILIC ANTICANCER DRUG COMPOUNDS, COMPOSITIONS AND RELATED METHODS

CROSS-REFERENCES TO RELATED APPLICATIONS

This application claims the benefit of U.S. Provisional Application No. 60/751,219, filed Dec. 16, 2005, and U.S. Provisional Application No. 60/753,967, filed Dec. 23, 2005, each application which is incorporated herein by referenced in its entirety.

BACKGROUND OF THE INVENTION

The ability to administer biologically effective drugs that are poorly soluble in biocompatible solvents to mammals has been a major hurdle in the realm of pharmaceutical and medicinal chemistry. In particular, difficulties arise when an active drug is either insoluble in water or unstable in other biocompatible solvents. Solubility problems are common and often cause delays in drug development. Several technologies have been developed to facilitate the delivery of poorly soluble and insoluble compounds. Examples of technologies specifically designed to solve solubility problems include complexing agents, nanoparticles, microemulsions, solubility enhancing formulations, prodrugs and water soluble prodrugs, and novel polymer systems.

One way to improve the solubility of medicinal agents is to chemically modify them or conjugate them to another molecule to alter the solubility profile in a particular solvent. Conjugates of active drugs, often referred to as prodrugs, include a chemical derivative of a biologically-active parent compound. Prodrugs may be biologically inert or maintain activity that is substantially less than the parent or active compound. The parent compound is released from the prodrug in vivo by a variety of mechanisms, including, for example, hydrolysis or enzymatic cleavage. The rate of release is influenced by several factors, including the type of chemical bond joining the active parent drug to the conjugate moiety.

Potent drugs that are poorly soluble in water include camptothecin and its analogs, taxanes (e.g., paclitaxel, docetaxel), candesartan, amphotericin B, azathioprine, cyclosporine, entacapone, danazol, eletriptan, and bosentan, to name a few. There continues to be a need for new methods, which are both safe and effective, of solubilizing and delivering poorly soluble active drug molecules.

SUMMARY OF THE INVENTION

In one aspect, the present invention provides lipophilic anticancer drug compounds that have been modified to increase their lipophilicity. The compounds of the invention include an anticancer drug compound and a lipophilic moiety. The anticancer drug compound is covalently coupled to the lipophilic moiety either directly or by a linker moiety to form a lipophilic anticancer drug compound. In one embodiment, the lipophilic anticancer drug compounds have the formula:

R-A-D wherein,
R is a lipophilic moiety selected from the group consisting of:
(a) substituted and unsubstituted alkyl,
(b) substituted and unsubstituted branched alkyl,
(c) substituted and unsubstituted heteroalkyl,
(d) substituted and unsubstituted cycloalkyl,
(e) substituted and unsubstituted alkenyl,
(f) substituted and unsubstituted alkynyl,
(g) substituted and unsubstituted aryl, and
(h) substituted and unsubstituted aralkyl;

A is a linker moiety selected from the group consisting of:
(a) —O—,
(b) —NR$_1$—,
(c) —S(=O)—,
(d) —SO$_2$—,
(e) —SO$_2$O—,
(f) —OSO$_2$O—,
(g) —SONR$_1$—,
(h) —SO$_2$NR$_1$—,
(i) —OSO$_2$NR$_1$—,
(j) —C(=O)—,
(k) —C(=O)O—,
(l) —OC(=O)O—,
(m) —C(=O)NR$_1$—,
(n) —OC(=O)NR$_1$—,
(o) —C(=O)OC(=O)—,
(p) —C(=O)OC(=O)O—,
(q) —OC(=O)OC(=O)O—,
(r) —NR$_1$C(=O)O—,
(s) —NR$_1$C(=O)NR$_2$—,
(t) —P(=O)(OR$_1$)O—,
(u) —OP(=O)(OR$_1$)O—,
(v) —P(=O)(NR$_1$)O—,
(w) —OP(=O)(NR$_1$)O—, and
(x) —BR'B'—, wherein R$_1$ and R$_2$ are independently selected from hydrogen, C$_{1-6}$ n-alkyl, C$_{3-12}$ branched alkyl, substituted or unsubstituted C$_{3-6}$ cycloalkyl, substituted or unsubstituted aryl, and substituted or unsubstituted aralkyl, wherein R' is independently selected from substituted or unsubstituted alkylene, substituted or unsubstituted heteroalkylene, substituted or unsubstituted branched alkylene, substituted or unsubstituted cycloalkylene, substituted or unsubstituted alkenylene, substituted or unsubstituted alkynylene, substituted or unsubstituted arylene, and substituted or unsubstituted aralkylene, and wherein B and B' are independently selected from the group consisting of:
(a) —O—,
(b) —NR$_3$—,
(c) —S(=O)—,
(d) —SO$_2$—,
(e) —SO$_2$O—,
(f) —OSO$_2$O—,
(g) —SONR$_3$—,
(h) —SO$_2$NR$_3$—,
(i) —OSO$_2$NR$_3$—,
(j) —C(=O)—,
(k) —C(=O)O—,
(l) —OC(=O)O—,
(m) —C(=O)NR$_3$—,
(n) —OC(=O)NR$_3$—,
(o) —C(=O)OC(=O)—,
(p) —C(=O)OC(=O)O—,
(q) —OC(=O)OC(=O)O—,
(r) —NR$_3$C(=O)O—,
(s) —NR$_3$C(=O)NR$_4$—,
(t) —P(=O)(OR$_3$)O—,
(u) —OP(=O)(OR$_3$)O—,
(v) —P(=O)(NR$_3$)O—, and
(w) —OP(=O)(NR$_3$)O—, wherein $R_3$ and $R_4$ are independently selected from hydrogen, $C_{1-6}$ n-alkyl, $C_{3-12}$ branched alkyl, substituted or unsubstituted $C_{3-6}$ cycloalkyl, substituted or unsubstituted aryl, and substituted or unsubstituted aralkyl; and D is an anticancer drug moiety.

In another aspect of the invention, compositions that include the compounds of the invention are provided. In one embodiment, the composition includes a compound of the invention, optionally one or more other therapeutic agents, and a lipophilic medium. Methods for making the compositions are also provided.

In a further aspect, the invention provides emulsion and micelle formulations that include a compound of the invention. The emulsion formulations include an oil phase and an aqueous phase. The emulsion may be an oil-in-water emulsion or a water-in-oil emulsion. The micelle formulation includes a compound of the invention and an aqueous phase. Methods for making the emulsion and micelle formulations are also provided.

In other aspects, methods for administering the compounds of the invention to a subject in need thereof, and methods for treating a condition treatable by administration of a compound of the invention are also provided.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
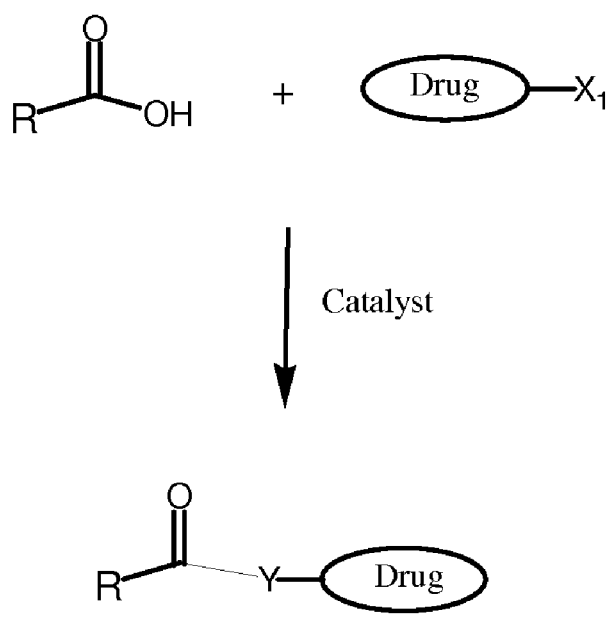
FIG. 1 schematically illustrates a lipophilic molecule containing a carboxyl group directly conjugated with an anticancer drug molecule containing at least one hydroxyl group or amino group or carboxyl to form a lipophilic anticancer drug compound; $X_1$ is a hydroxyl group, carboxyl group, or amino group; Y is an oxygen atom, —$NR_1$, or carboxy group. $R_1$ is selected from H, $C_{1-6}$ n-alkyl, $C_{3-12}$ branched alkyl, substituted or unsubstituted $C_{3-6}$ cycloalkyl, substituted or unsubstituted aryl, or substituted or unsubstituted aralkyl. R is selected from substituted or unsubstituted alkyl, substituted or unsubstituted heteroalkyl, substituted or unsubstituted branched alkyl, substituted or unsubstituted cycloalkyl, substituted or unsubstituted alkynyl, substituted or unsubstituted alkenyl, substituted or unsubstituted aryl, substituted or unsubstituted aralkyl, or any combination of the aforementioned groups.

In one aspect, the present invention provides anticancer drug compounds that have been modified to increase their lipophilicity. The compounds of the invention are lipophilic anticancer drug compounds. The compounds of the invention include an anticancer drug moiety and a lipophilic moiety. The lipophilic moiety is a lipophilic group.

In some embodiments, the anticancer drug moiety is covalently coupled to the lipophilic moiety through a linker moiety. In other embodiments, the anticancer drug moiety is directly covalently coupled to the lipophilic moiety without a linker moiety. Methods for making the lipophilic anticancer drug compounds are provided.

In another aspect of the invention, compositions that include one or more of the lipophilic anticancer drug compounds of the invention are provided. In one embodiment, the composition includes a lipophilic medium. In one embodiment, the lipophilic medium is a tocopherol. As used herein, the term "tocopherol" refers to a family of natural or synthetic compounds, also known by their generic names, tocol or vitamin E. In addition to tocopherol compounds, tocotrienol compounds are included in this family. Tocol compounds have a phenolic alcohol (C-6) chroman head and a phytyl tail (C-2). Tocopherols constitute a series of related benzopyranols (or methyl tocols) in which the C-2 phytyl (sixteen carbon) side chain is saturated. Representative tocopherols include α-tocopherol, (d-form, dl-form, l-form), β-tocopherol (d-form, dl-form, l-form), γ-tocopherol (d-form, dl-form, l-form), and δ-tocopherol (d-from, dl-form, l-form). Tocotrienols are similar in structure to tocopherols except that the trienols have three double bonds in the C-2 phytyl side chain. Representative tocotrienols include α-tocotrienol, (d-form, dl-form, l-form), β-tocotrienol (d-form, dl-form, l-form), γ-tocotrienol (d-form, dl-form, l-form), and δ-tocotrienol (d-from, dl-form, l-form). Methods for making the compositions are also provided.

In a further aspect, the invention provides emulsions that include one or more of the lipophilic anticancer drug compounds. In one embodiment, the emulsion includes a lipophilic anticancer drug compound, a lipophilic medium in which the lipophilic anticancer drug compound is soluble, and an aqueous medium. The emulsion may be an oil-in-water emulsion or a water-in-oil emulsion. In one embodiment, the lipophilic medium is a tocopherol or a tocotrienol. Methods for making the lipophilic anticancer drug compound-containing emulsions are also provided.

In another aspect, the invention provides micelle formulations that include one or more of the lipophilic anticancer drug compounds. In one embodiment, the micelle formulation includes a lipophilic anticancer drug compound, one or more solvents in which the modified lipophilic anticancer drug compound is soluble, one or more surfactants, and an aqueous medium.

In one embodiment, a lipophilic anticancer drug compound of the invention may be represented by formula:

R-A-D in which R is a lipophilic moiety, D is an anticancer drug moiety, and A is a functional group or linker moiety.

As used herein, the term "lipophilic moiety," refers to a lipophilic group. Examples of suitable lipophilic group, include, for example, substituted or unsubstituted alkyl, substituted or unsubstituted heteroalkyl, substituted or unsubstituted branched alkyl, substituted or unsubstituted cycloalkyl, substituted or unsubstituted alkynyl, substituted or unsubstituted alkenyl, substituted or unsubstituted aryl, substituted or unsubstituted aralkyl, or any combination of the aforementioned groups. A lipophilic moiety is covalently coupled to an anticancer drug molecule by a functional group or linker to provide a lipophilic anticancer drug compound of the invention.

As used herein, the term "anticancer drug moiety" refers to an anticancer drug compound that can be covalently coupled to a lipophilic moiety to provide a lipophilic anticancer compound of the invention.

Anticancer drug compounds selected for conjugation need not be substantially water-insoluble, although the lipophilic anticancer drug compounds of the present invention are especially well suited for formulating and delivering such water-insoluble compounds. The lipophilic anticancer drug compounds of the invention provide for the solubilization of anticancer drug compounds in pharmaceutical formulations that would be otherwise difficult to formulate for administration. The lipophilic anticancer drug compounds of the invention also provide for enhanced pharmacokinetic properties compared to the unmodified anticancer drug compounds (i.e., parent compounds). For example, while some anticancer drug compounds are rapidly cleared from a subject shortly after administration (e.g., highly water-soluble anticancer drug compounds), the lipophilic anticancer drug compounds of the invention offer advantages associated with relatively slow clearance. The lipophilic anticancer drug compounds of the invention also provide for distribution properties after administration to a subject that may differ significantly and advantageously compared to the unmodified anticancer drug compounds (parent drug compounds).

Representative anticancer drug compounds useful in making the lipophilic anticancer drug compounds of the invention include camptothecin, and camptothecin derivatives.

As used herein, "functional group" and "linker moiety" refer to an atom or a group of atoms that covalently link the lipophilic moiety to anticancer drug compound moiety.

"A", a functional group or a linker, is independently selected from the group consisting of
a) —O—
b) —NR$_1$—
c) —S(=O)—,
d) —SO$_2$—,
e) —SO$_2$O—,
f) —OSO$_2$O—,
g) —SONR$_1$—
h) —SO$_2$NR$_1$—
i) —OSO$_2$NR$_1$—
j) —C(=O)—,
k) —C(=O)O—,
l) —OC(=O)O—
m) —C(=O)NR$_1$—,
n) —OC(=O)NR$_1$—,
o) —C(=O)OC(=O)—,
p) —C(=O)OC(=O)O—,
q) —OC(=O)OC(=O)O—,
r) —NR$_1$C(=O)O—,
s) —NR$_1$C(=O)NR$_2$—,
t) —P(=O)(OR$_1$)O—,
u) —OP(=O)(OR$_1$)O—,
v) —P(=O)(NR$_1$)O—,
w) —OP(=O)(NR$_1$)O—,
x) —BR'B'— wherein R$_1$ and R$_2$ are independently selected from H, C$_{1-6}$ n-alkyl, C$_{3-12}$ branched alkyl, substituted or unsubstituted C$_{3-6}$ cycloalkyl, substituted or unsubstituted aryl, and substituted or unsubstituted aralkyl.

—BR'B'— is a linker, wherein R' is independently selected from substituted or unsubstituted alkylene, substituted or unsubstituted heteroalkylene, substituted or unsubstituted branched alkylene, substituted or unsubstituted cycloalkylene, substituted or unsubstituted alkynylene, substituted or unsubstituted alkenylene, substituted or unsubstituted arylene, substituted or unsubstituted aralkylene, or any combination of aforementioned groups;

wherein B and B' are functional groups or linkers and independently selected from the group consisting of
a) —O—
b) —NR$_3$—
c) —S(=O)—,
d) —SO$_2$—,
e) —SO$_2$O—,
f) —OSO$_2$O—,
g) —SONR$_3$—
h) —SO$_2$NR$_3$—
i) —OSO$_2$NR$_3$—
j) —C(=O)—,
k) —C(=O)O—,
l) —OC(=O)O—
m) —C(=O)NR$_3$—,
n) —OC(=O)NR$_3$—,
o) —C(=O)OC(=O)—,
p) —C(=O)OC(=O)O—,
q) —OC(=O)OC(=O)O—,
r) —NR$_3$C(=O)O—,
s) —NR$_3$C(=O)NR$_4$—,
t) —P(=O)(OR$_3$)O—,
u) —OP(=O)(OR$_3$)O—,
v) —P(=O)(NR$_3$)O—,
w) —OP(=O)(NR$_3$)O—, wherein R$_3$ and R$_4$ are independently selected from H, C$_{1-6}$ n-alkyl, C$_{3-12}$ branched alkyl, substituted or unsubstituted C$_{3-6}$ cycloalkyl, substituted or unsubstituted aryl, and substituted or unsubstituted aralkyl.

In one embodiment, the anticancer drug moiety may be selected from camptothecin, 10-hydroxycamptothecin, 7-ethyl-10-hydroxycamptothecin, 9-aminocamptothecin, 9-amino-7-ethylcamptothecin, 10-aminocamptothecin, 10-amino-7-ethylcamptothecin, and other camptothecin derivative.

In one embodiment, D has the formula

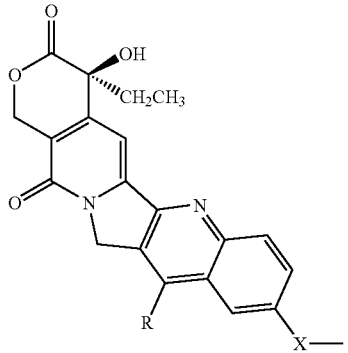

wherein R is selected from the group consisting of H and CH$_2$CH$_3$, and X is selected from the group consisting of O and NH.

In one embodiment, D has the formula

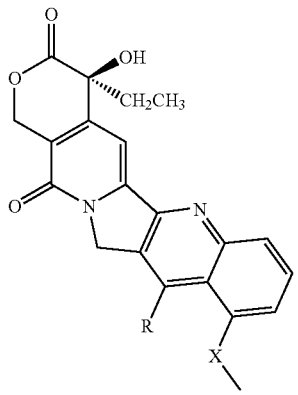

wherein R is selected from the group consisting of H and CH$_2$CH$_3$, and X is selected from the group consisting of O and NH.

In one embodiment, D has the formula

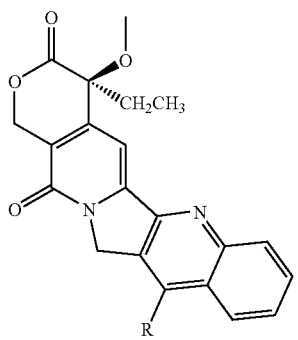

wherein R is selected from the group consisting of H and CH$_2$CH$_3$.

In one embodiment, D has the formula

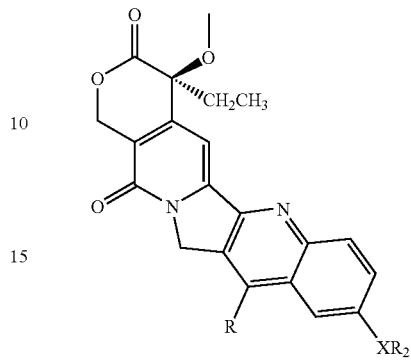

wherein R is selected from the group consisting of H and CH$_2$CH$_3$; X is selected from the group consisting of O and NH; and R$_2$ is selected from the group consisting of H, acyl, alkyl, branched alkyl, substituted or unsubstituted cycloalkyl, substituted or unsubstituted aryl, and substituted or unsubstituted aralkyl.

In one embodiment, D has the formula

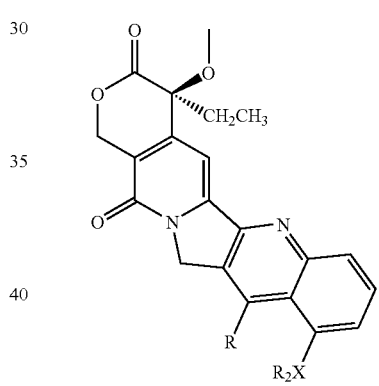

wherein R is selected from the group consisting of H and CH$_2$CH$_3$; X is selected from the group consisting of O and NH; R$_2$ is selected from the group consisting of H, acyl, alkyl, branched alkyl, substituted or unsubstituted cycloalkyl, substituted or unsubstituted aryl, and substituted or unsubstituted aralkyl.

Representative lipophilic anticancer drug compounds of the invention include 10-(benzyl succinate)-7-ethylcamptothecin, 20-(benzyl succinate)camptothecin, 10-(benzyl 3,3-tetramethyleneglutarate)-7-ethylcamptothecin, 20-(benzyl 3,3-tetramethyleneglutarate)camptothecin, 10-(4-methylbenzyl succinate)-7-ethylcamptothecin, 10-(2,4,6-trimethylbenzyl succinate)-7-ethylcamptothecin, 10-(2,3,4,5,6-pentamethylbenzyl succinate)-7-ethylcamptothecin, 10-(1-octyl succinate)-7-ethylcamptothecin, 20-(1-octyl succinate)camptothecin, 10-octanoyloxy-7-ethylcamptothecin, 10-(N-n-butyl carbamate)-7-ethylcamptothecin, 10-(N-t-butyl carbamate)-7-ethylcamptothecin, 10-(4-butoxybenzoyloxy)-7-ethylcamptothecin, 10-(n-butyl carbonoyloxy)-7-ethylcamptothecin, 10-benzyloxy-7-ethylcamptothecin.

As used herein, the term "alkyl" refers to straight chain and branched alkyl groups, typically having from 1 to 20 carbon atoms. Cycloalkyl groups include monocyclic and polycyclic alkyl groups, monocyclic alkyl groups typically having from about 3 to about 8 carbon atoms in the ring.

The term "aryl" refers to monocyclic and polycyclic aromatic compounds having from 6 to 14 carbon or hetero atoms, and includes carbocyclic aryl groups and heterocyclic aryl groups. Representative aryl groups include phenyl, naphthyl, pyridinyl, pyrimidinyl, thiazolyl, indolyl, imidazolyl, furanyl, and the like. As used herein, the term "aryl" includes heteroaryl groups. The term "aralkyl" refers to an alkyl group that is substituted with an aryl group.

The term "acyl" refers to a —C(=O)R group, where R is a substituted or unsubstituted alkyl, substituted or unsubstituted cycloalkyl, substituted or unsubstituted heteroalkyl, substituted or unsubstituted aryl, substituted or unsubstituted heteroaryl, or substituted or unsubstituted aralkyl group.

The term "substituted" refers to a substituent in which one or more hydrogen atoms is replaced with another group such as, for example, alkyl, cycloalkyl, heteroalkyl, aryl, heteroaryl, halogen, amino, thio, nitro, and alkoxy.

In another aspect of the invention, methods for making lipophilic anticancer drug compounds are provided. A lipophilic molecule can be covalently coupled to an anticancer drug compound to form a lipophilic anticancer drug compound.

In a representative embodiment, a carboxyl group of a lipophilic molecule is directly coupled with a hydroxyl group or amino group or a carboxyl group of an anticancer drug compound to form a lipophilic anticancer drug compound. Such a method is illustrated schematically in FIG. 1. In FIG. 1, $X_1$ is a hydroxyl group, carboxyl group, or amino group; Y is an oxygen atom, —$NR_1$, or carboxy group. $R_1$ is selected from H, $C_{1-6}$ n-alkyl, $C_{3-12}$ branched alkyl, substituted or unsubstituted $C_{3-6}$ cycloalkyl, substituted or unsubstituted aryl, or substituted or unsubstituted aralkyl. R is the lipophilic moiety, independently selected from substituted or unsubstituted alkyl, substituted or unsubstituted heteroalkyl, substituted or unsubstituted branched alkyl, substituted or unsubstituted cycloalkyl, substituted or unsubstituted alkynyl, substituted or unsubstituted alkenyl, substituted or unsubstituted aryl, substituted or unsubstituted aralkyl or any combination of the aforementioned groups.

In another embodiment, a lipophilic molecule containing a hydroxyl group or amino group may be functionalized with a reagent, for example, 2-chloroacetic acid, succinic acid anhydride, phthalic anhydride, isophthalic acid, terephthalic acid, epichlorohydrin, phosphorous oxychloride, alkyl dichlorophosphate, aryl dichlorophosphate, alkyl phosphonic dichloride, aryl phosphonic dichloride, chlorosulfonic acid, or 4-isocyanatobenzoyl chloride. The functional group added to the lipophilic molecule may be, for example, a carboxyl group (—COOH), oxiranyl group (—CH(O)$CH_2$), phosphoric chloride group (—P(O)ORCl), phosphonic chloride group (—P(O)RCl), chlorosulfonic group (—$SO_2$Cl), isocyanato group (—N=C=O), carbonyl chloride group (—COCl). The resulting carboxyl group, oxiranyl group, isocyanato group, or acid chloride group can then be reacted with anticancer drug compound or functionalized anticancer drug compound to provide a lipophilic anticancer drug compound.

Figure 2:
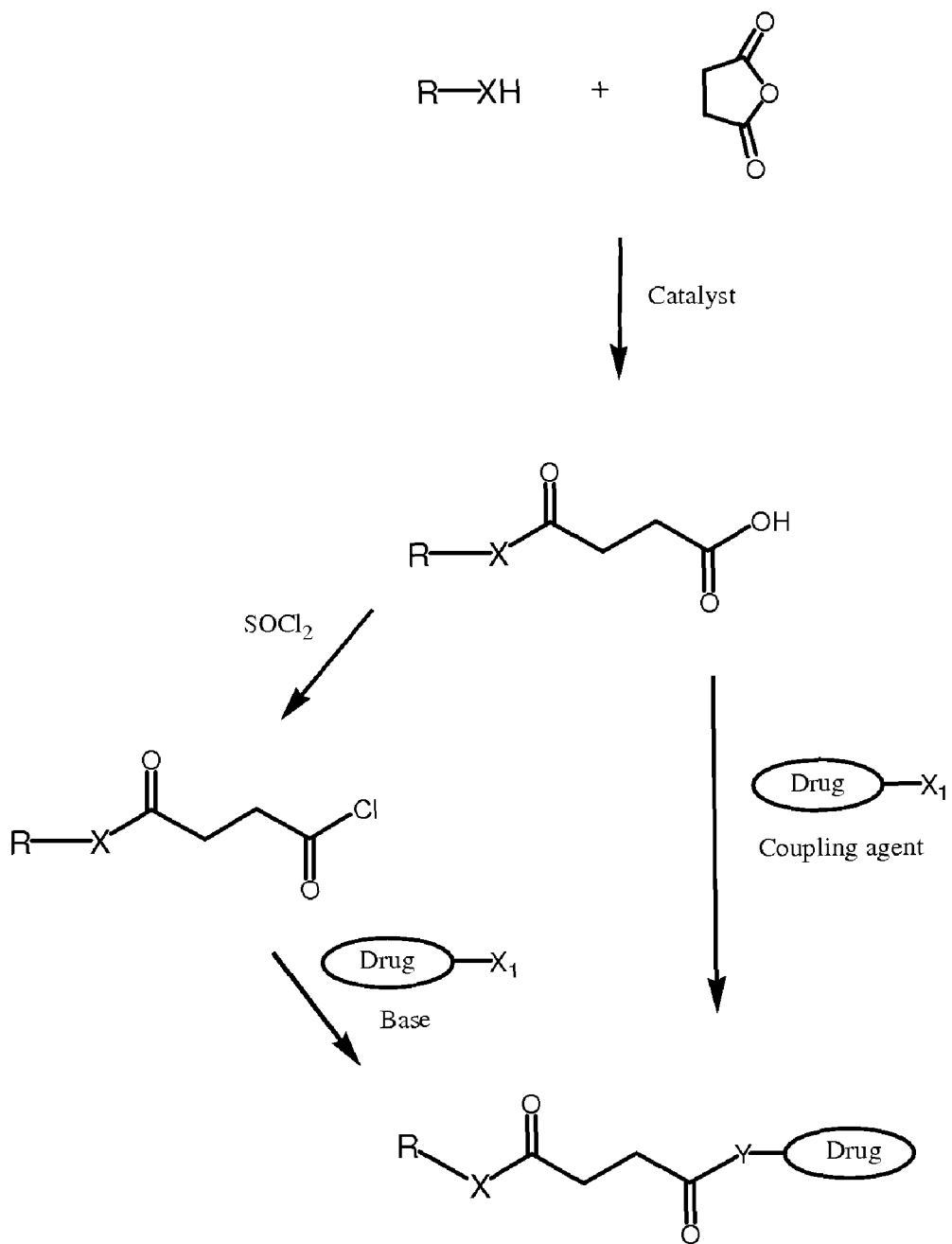
FIG. 2 schematically illustrates a lipophilic molecule functionalized with a carboxyl group (—COOH), and reaction of the resulting acid with an anticancer drug compound that contains at least one functional group or an appropriately functionalized anticancer drug compound to provide a lipophilic anticancer drug compound; X is an oxygen atom, or —$NR_1$ group; $X_1$ is a hydroxyl group, carboxyl group, or amino group; Y is an oxygen atom, —$NR_2$, or carboxy group; $R_1$ and $R_2$ are independently selected from H, $C_{1-6}$ n-alkyl, $C_{3-12}$ branched alkyl, substituted or unsubstituted $C_{3-6}$ cycloalkyl, substituted or unsubstituted aryl, or substituted or unsubstituted aralkyl; R is selected from substituted or unsubstituted alkyl, substituted or unsubstituted heteroalkyl, substituted or unsubstituted branched alkyl, substituted or unsubstituted cycloalkyl, substituted or unsubstituted alkynyl, substituted or unsubstituted alkenyl, substituted or unsubstituted aryl, substituted or unsubstituted aralkyl, or any combination of the aforementioned groups.

In a representative embodiment, a lipophilic molecule containing a hydroxyl or amino group reacts with succinic acid anhydride to form a succinic acid derivative which couples with the hydroxyl, amine, or carboxyl group of the anticancer drug compound to form a lipophilic anticancer drug compound. Such a method is illustrated schematically in FIG. 2. In FIG. 2, X may be O atom, or —$NR_1$ group, $X_1$ may be —OH, —$NH_2$, —NHR, or —$CO_2$H, and Y may be O, —NH, —$NHR_2$, or —C(=O)O—, and $R_1$ and $R_2$ are independently selected from H, $C_{1-6}$ n-alkyl, $C_{3-12}$ branched alkyl, substituted or unsubstituted $C_{3-6}$ cycloalkyl, substituted or unsubstituted aryl, or substituted or unsubstituted aralkyl; R is selected from substituted or unsubstituted alkyl, substituted or unsubstituted heteroalkyl, substituted or unsubstituted branched alkyl, substituted or unsubstituted cycloalkyl, substituted or unsubstituted alkynyl, substituted or unsubstituted alkenyl, substituted or unsubstituted aryl, substituted or unsubstituted aralkyl, or any combination of the aforementioned groups.

The syntheses of representative lipophilic anticancer drug compounds of the invention are illustrated in FIGS. 3-16 and described in Examples 1 to 15.

Figure 3:
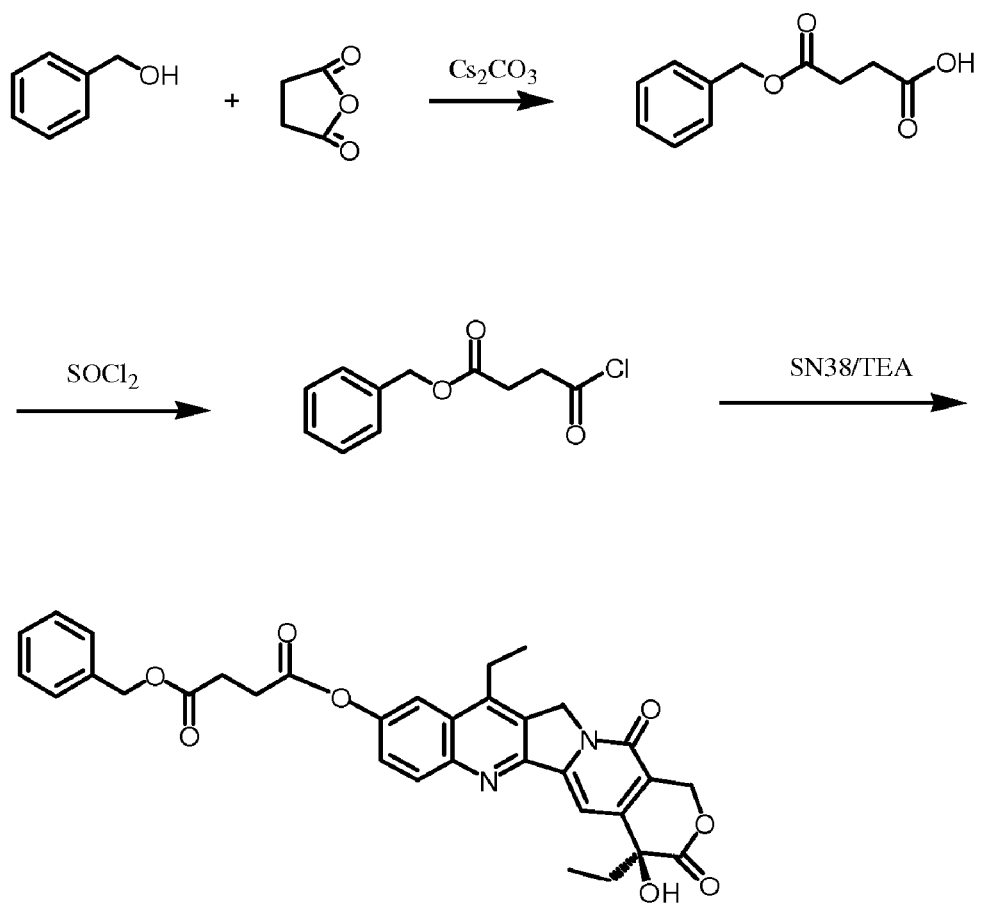
FIG. 3 schematically illustrates the preparation of 10-(benzyl succinate)-7-ethylcamptothecin.

FIG. 3 illustrates the preparation of 10-(benzyl succinate)-7-ethylcamptothecin. As used herein, 10-(benzyl succinate)-7-ethylcamptothecin refers to butanedioic acid, benzyl (4S)-4,11-diethyl-3,4,12,14-tetrahydro-4-hydroxy-3,14-dioxo-1H-pyrano[3',4':6,7]indolizino[1,2-b]quinolin-9-yl ester. A free carboxyl group is attached to the hydroxyl group of benzyl alcohol using succinic acid anhydride and a catalyst such as cesium carbonate. The free carboxyl group is converted to a carbonyl chloride group which is then coupled to the hydroxyl group at C-10 of 7-ethyl-10-hydroxycamptothecin (SN38) in the presence of a base such as triethylamine to provide 10-(benzyl succinate)-7-ethylcamptothecin. The preparation 10-(benzyl succinate)-7-ethylcamptothecin is described in Example 1.

Figure 4:
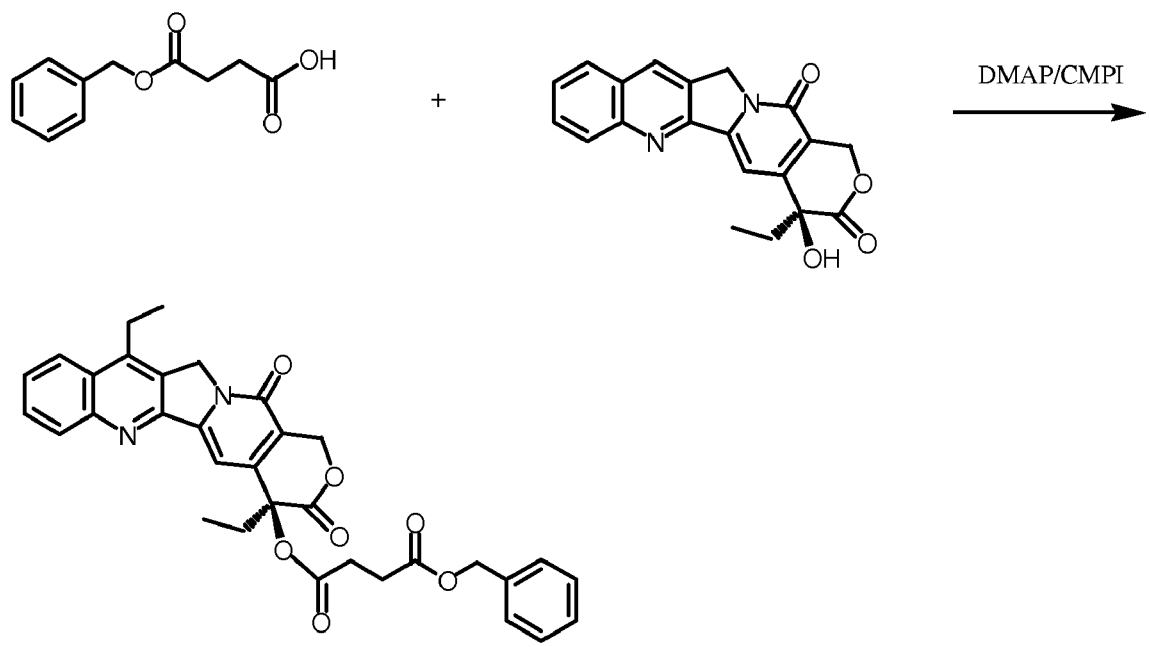
FIG. 4 schematically illustrates the preparation of 20-(benzyl succinate)-camptothecin.

FIG. 4 illustrates the preparation of 20-(benzyl succinate) camptothecin. As used herein, 20-(benzyl succinate)camptothecin refers to butanedioic acid, benzyl (4S)-4-ethyl-3,4,12,14-tetrahydro-3,14-dioxo-1H-pyrano[3',4':6,7]indolizino[1,2-b]quinolin-4-yl ester. Benzyl succinic acid reacts with camptothecin in the presence of coupling agents, 2-chloro-1-methylpyridinium iodide (CMPI) and 4-(dimethylamino)pyridine (DMAP). The preparation of 20-(benzyl succinate) camptothecin is described in Example 2.

Figure 5:
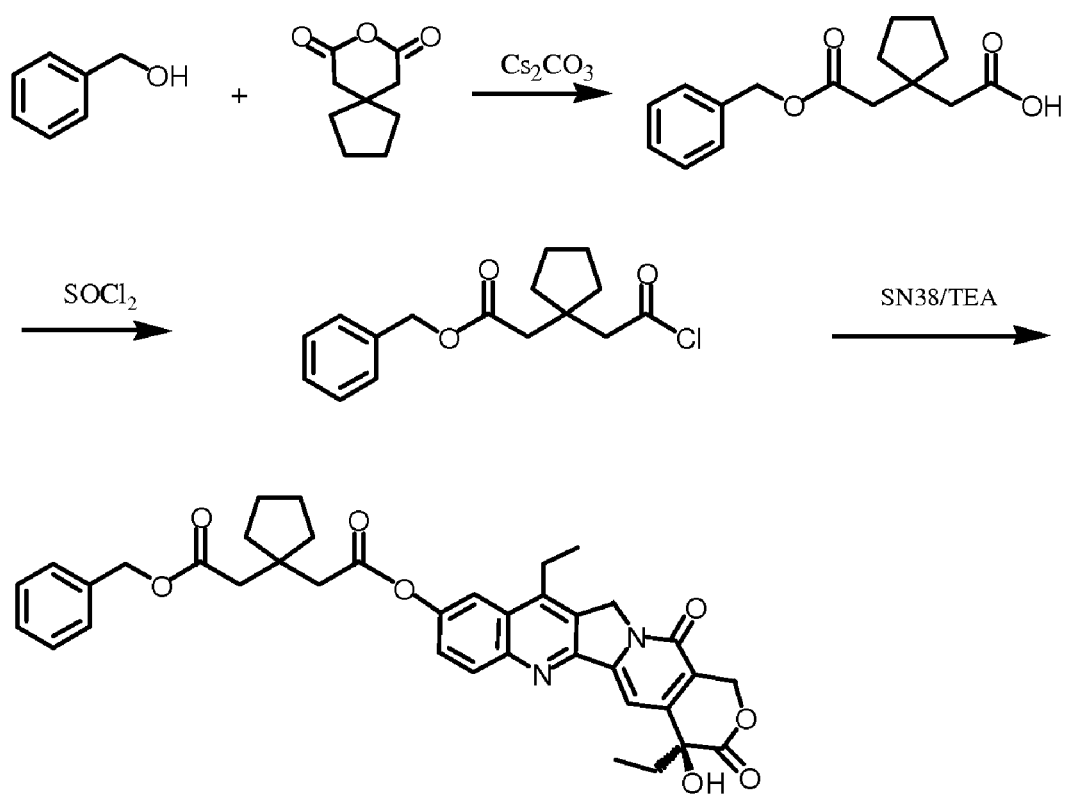
FIG. 5 schematically illustrates the preparation of 10-(benzyl 3,3-tetramethyleneglutarate)-7-ethylcamptothecin.

FIG. 5 illustrates the preparation of 10-(benzyl 3,3-tetramethyleneglutarate)-7-ethylcamptothecin. As used herein, 10-(benzyl 3,3-tetramethyleneglutarate)-7-ethylcamptothecin refers to 3,3-tetramethyleneglutaric acid, benzyl (4S)-4,11-diethyl-3,4,12,14-tetrahydro-4-hydroxy-3,14-dioxo-1H-pyrano[3',4':6,7]indolizino[1,2-b]quinolin-9-yl ester. Benzyl alcohol reacted with 3,3-tetramethyleneglutaric anhydride to form 3,3-tetramethyleneglutaric acid monobenzyl ester. The carboxyl group of the 3,3-tetramethyleneglutaric acid monobenzyl ester is converted to carbonyl chloride group by thionyl chloride, and then coupled with the hydroxyl group at C-10 of 7-ethyl-10-hydroxycamptothecin to form 10-(benzyl 3,3-tetramethyleneglutarate)-7-ethylcamptothecin. The preparation of 10-(benzyl 3,3-tetramethyleneglutarate)-7-ethylcamptothecin is described in Example 3.

Figure 6:
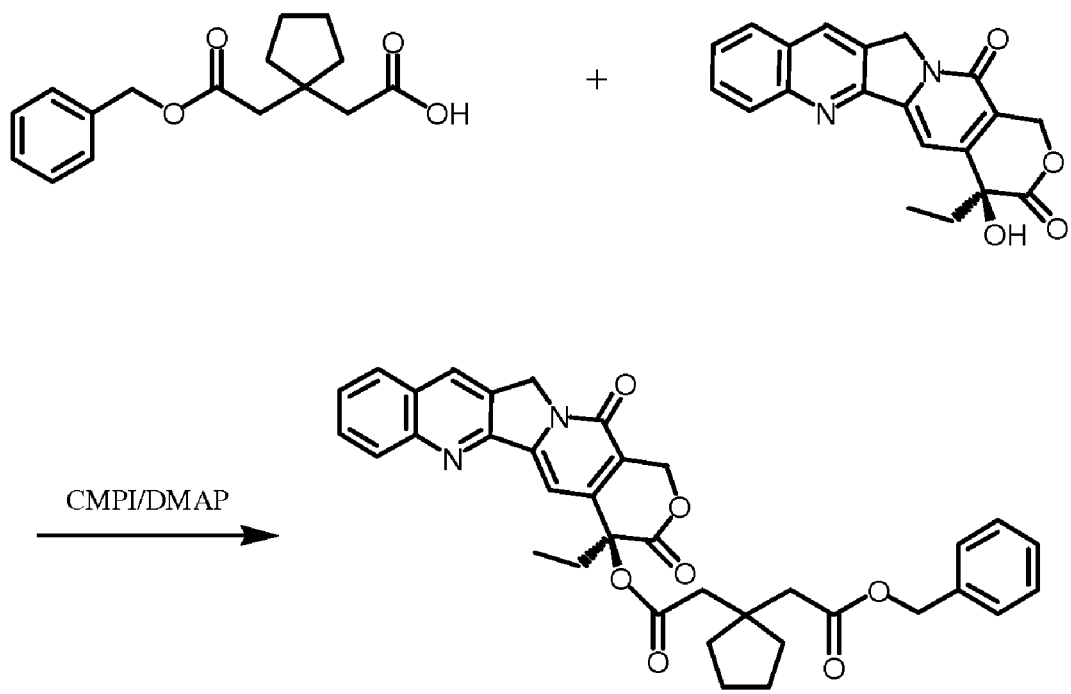
FIG. 6 schematically illustrates the preparation of 20-(benzyl 3,3-tetramethyleneglutarate)camptothecin.

FIG. 6 illustrates the preparation of 20-(benzyl 3,3-tetramethyleneglutarate)camptothecin. As used herein, 20-(benzyl 3,3-tetramethyleneglutarate)camptothecin refers to 3,3-tetramethyleneglutaric acid, benzyl (4S)-4-ethyl-3,4,12,14-tetrahydro-3,14-dioxo-1H-pyrano[3',4':6,7]indolizino[1,2-b] quinolin-4-yl ester. 3,3-tetramethyleneglutaric acid monobenzyl ester reacts with camptothecin in the presence of 2-chloro-1-methylpyridinium iodide (CMPI) and 4-(dimethylamino)pyridine as coupling agents to form 20-(benzyl 3,3-tetramethyleneglutarate)camptothecin. The preparation of 20-(benzyl 3,3-tetramethyleneglutarate)camptothecin is described in Example 4.

Figure 7:
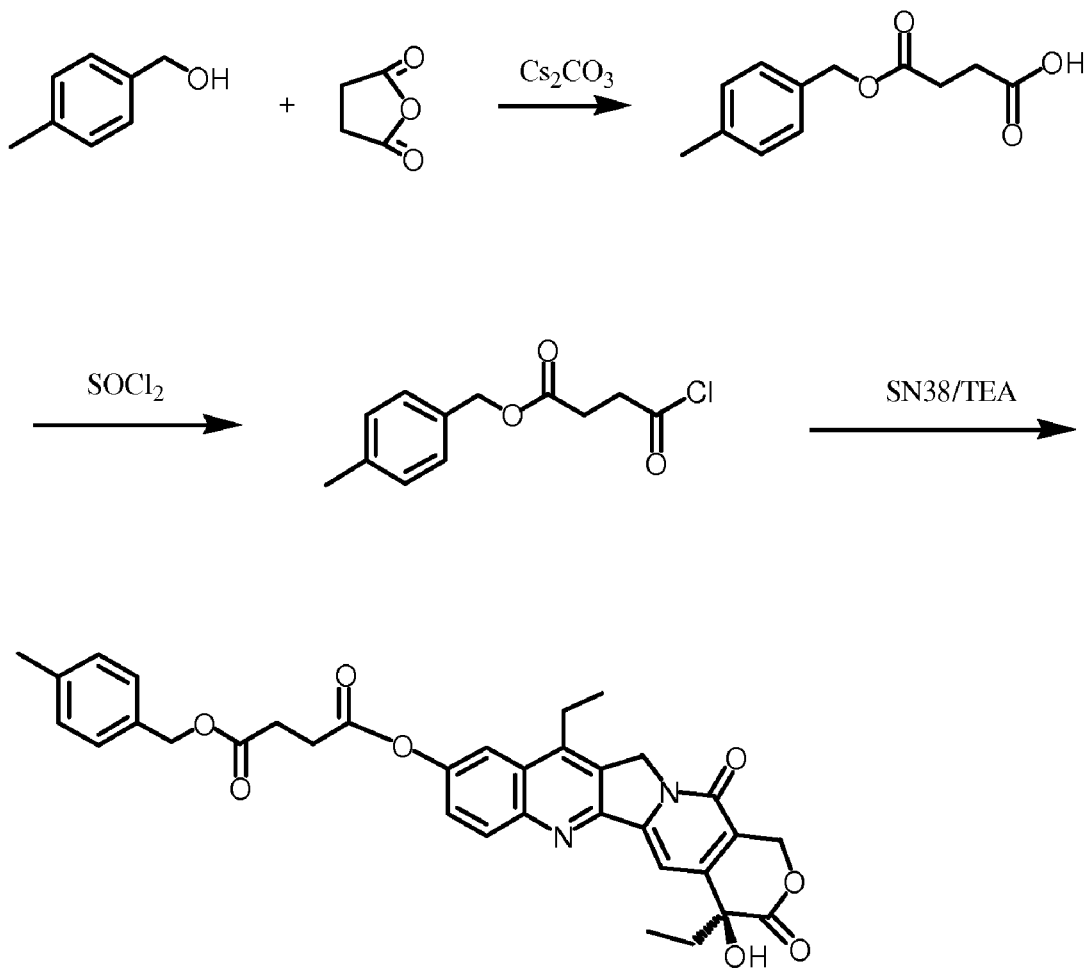
FIG. 7 schematically illustrates the preparation of 10-(4-methylbenzyl succinate)-7-ethylcamptothecin.

FIG. 7 illustrates the preparation of 10-(4-methylbenzyl succinate)-7-ethylcamptothecin. As used herein, 10-(4-methylbenzyl succinate)-7-ethylcamptothecin refers to butanedioic acid, (4S)-4,11-diethyl-3,4,12,14-tetrahydro-4-hydroxy-3,14-dioxo-1H-pyrano[3',4':6,7]indolizino[1,2-b]quinolin-9-yl 4-methylbenzyl ester. The synthetic method is similar to the preparation of 10-(benzyl succinate)-7-ethylcamptothecin. The preparation of 10-(4-methylbenzyl succinate)-7-ethylcamptothecin is described in Example 5.

Figure 8:
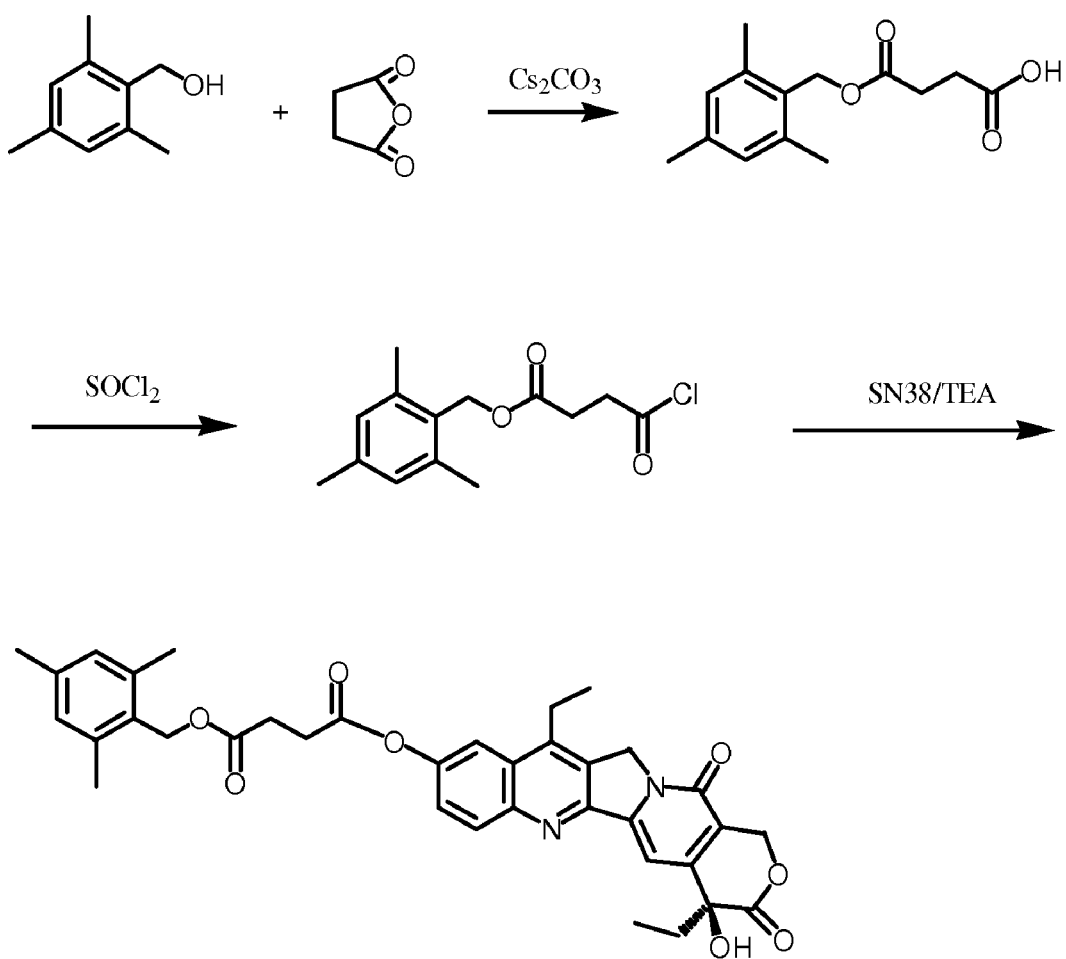
FIG. 8 schematically illustrates the preparation of 10-(2,4,6-trimethylbenzyl succinate)-7-ethylcamptothecin.

FIG. 8 illustrates the preparation of 10-(2,4,6-trimethylbenzyl succinate)-7-ethylcamptothecin. As used herein, 10-(2,4,6-trimethylbenzyl succinate)-7-ethylcamptothecin refers to butanedioic acid, (4S)-4,11-diethyl-3,4,12,14-tetrahydro-4-hydroxy-3,14-dioxo-1H-pyrano[3',4':6,7]indolizino[1,2-b]quinolin-9-yl 2,4,6-trimethylbenzyl ester. The preparation of 10-(2,4,6-trimethylbenzyl succinate)-7-ethylcamptothecin is described in Example 6.

Figure 9:
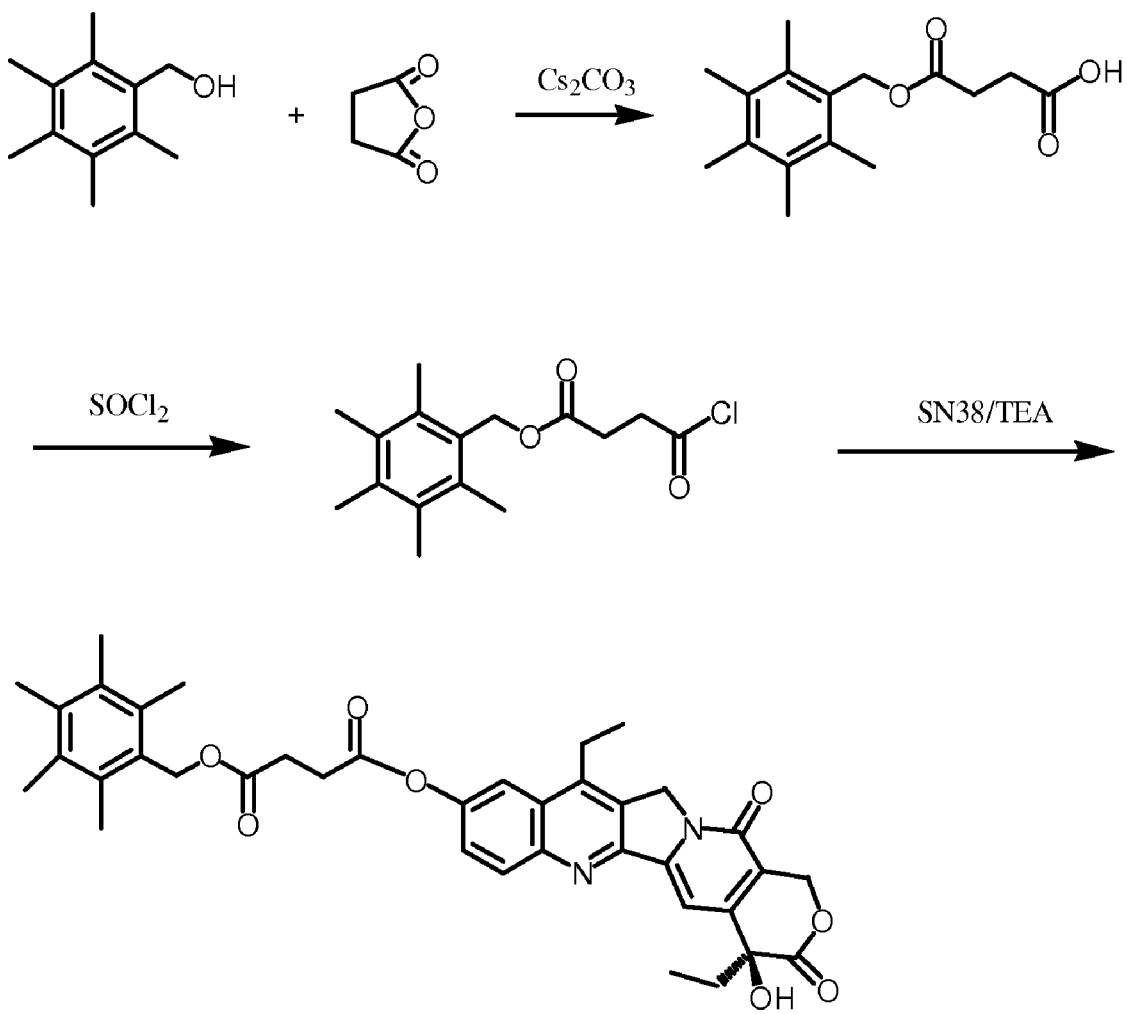
FIG. 9 schematically illustrates the preparation of 10-(2,3,4,5,6-pentamethylbenzyl succinate)-7-ethylcamptothecin.

FIG. 9 schematically illustrates the preparation of 10-(2,3,4,5,6-pentamethylbenzyl succinate)-7-ethylcamptothecin. As used herein, 10-(2,3,4,5,6-pentamethylbenzyl succinate)-7-ethylcamptothecin refers to butanedioic acid, (4S)-4,11-diethyl-3,4,12,14-tetrahydro-4-hydroxy-3,14-dioxo-1H-pyrano[3',4':6,7]indolizino[1,2-b]quinolin-9-yl 2,3,4,5,6-pentamethylbenzyl ester. The preparation of 10-(2,3,4,5,6-pentamethylbenzyl succinate)-7-ethylcamptothecin is described in Example 7.

Figure 10:
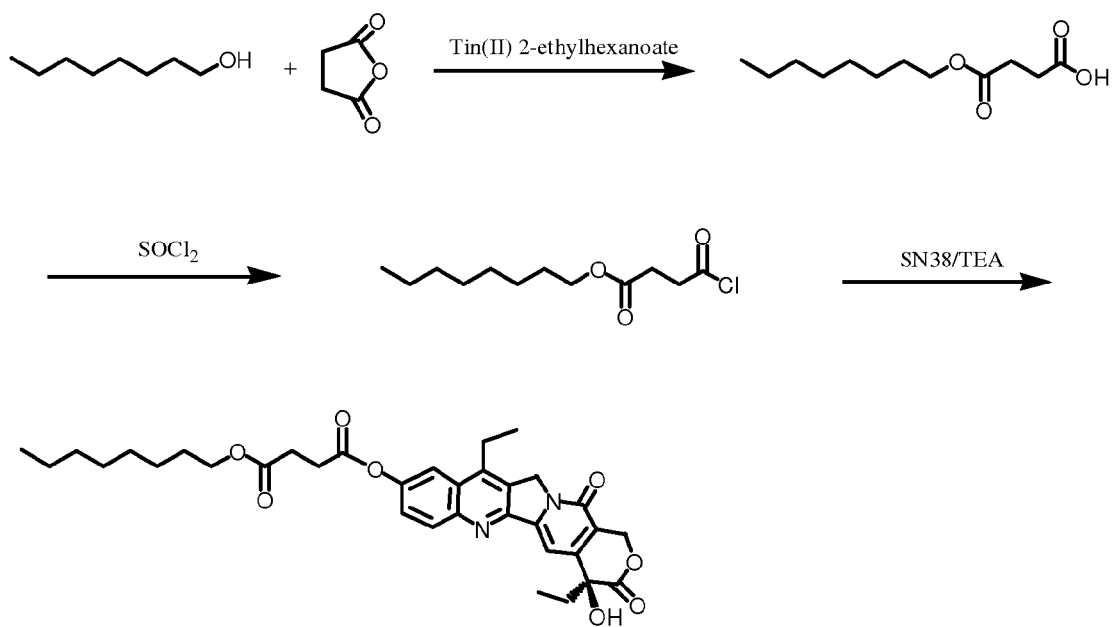
FIG. 10 schematically illustrates the preparation of 10-(1-octyl succinate)-7-ethylcamptothecin.

FIG. 10 schematically illustrates the preparation of 10-(1-octyl succinate)-7-ethylcamptothecin. As used herein, 10-(1-octyl succinate)-7-ethylcamptothecin refers to butanedioic acid, (4S)-4,11-diethyl-3,4,12,14-tetrahydro-4-hydroxy-3,14-dioxo-1H-pyrano[3',4':6,7]indolizino[1,2-b]quinolin-9-yl 1-octyl ester. The preparation of 10-(1-octyl succinate)-7-ethylcamptothecin is described in Example 8.

Figure 11:
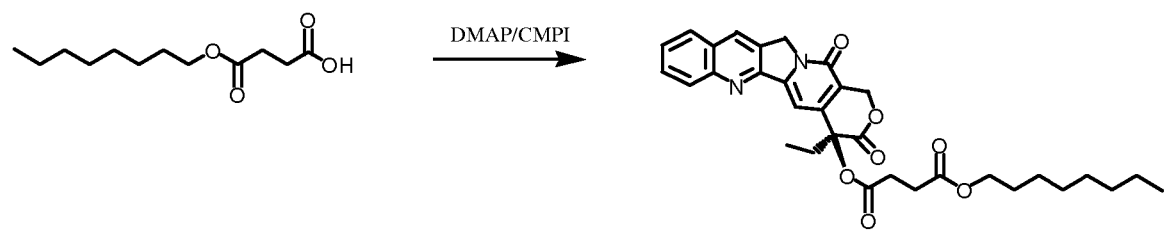
FIG. 11 schematically illustrates the preparation of 20-(1-octyl succinate)camptothecin.

FIG. 11 schematically illustrates the preparation of 20-(1-octyl succinate)camptothecin. As used herein, 20-(1-octyl succinate)camptothecin refers to butanedioic acid, (4S)-4-ethyl-3,4,12,14-tetrahydro-3,14-dioxo-1H-pyrano[3',4':6,7]indolizino[1,2-b]quinolin-4-yl 1-octyl ester. The preparation of 20-(1-octyl succinate)camptothecin is described in Example 9.

Figure 12:
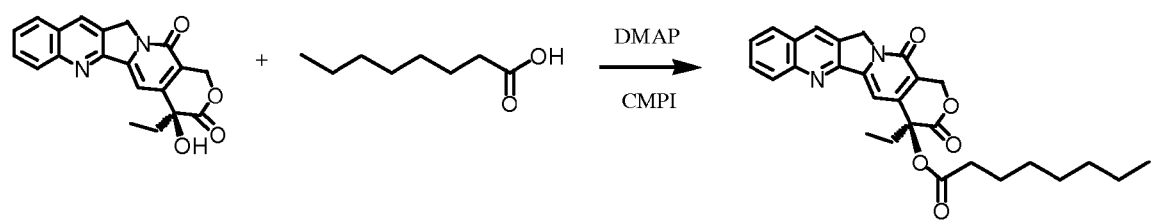
FIG. 12 schematically illustrates the preparation of 10-octanoyloxy-7-ethylcamptothecin.

FIG. 12 schematically illustrates the preparation of 10-octanoyloxy-7-ethylcamptothecin. As used herein, 10-octanoyloxy-7-ethylcamptothecin refers to octanoic acid, (4S)-4-ethyl-3,4,12,14-tetrahydro-3,14-dioxo-1H-pyrano[3',4':6,7]indolizino[1,2-b]quinolin-4-yl ester. The preparation of 10-octanoyloxy-7-ethylcamptothecin is described in Example 10.

Figure 13:
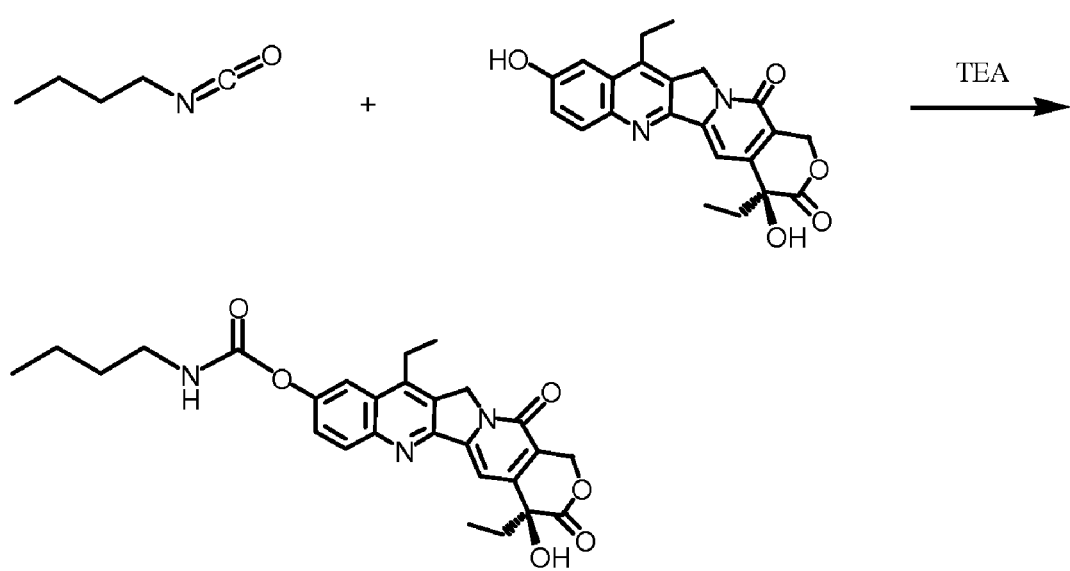
FIG. 13 schematically illustrates the preparation of 10-(N-n-butyl carbamate)-7-ethylcamptothecin.

FIG. 13 illustrates the preparation of 10-(N-n-butyl carbamate)-7-ethylcamptothecin. As used herein, 10-(N-n-butyl carbamate)-7-ethylcamptothecin refers to n-butyl-carbamic acid, (4S)-4,11-diethyl-3,4,12,14-tetrahydro-4-hydroxy-3,14-dioxo-1H-pyrano[3',4':6,7]indolizino[1,2-b]quinolin-9-yl ester. Butyl isocyanate reacts with 7-ethyl-10-hydroxycamptothecin in the presence of triethylamine to generate 10-(N-n-butyl carbamate)-7-ethylcamptothecin. The preparation of 10-(N-n-butyl carbamate)-7-ethylcamptothecin is described in Example 11.

Figure 14:
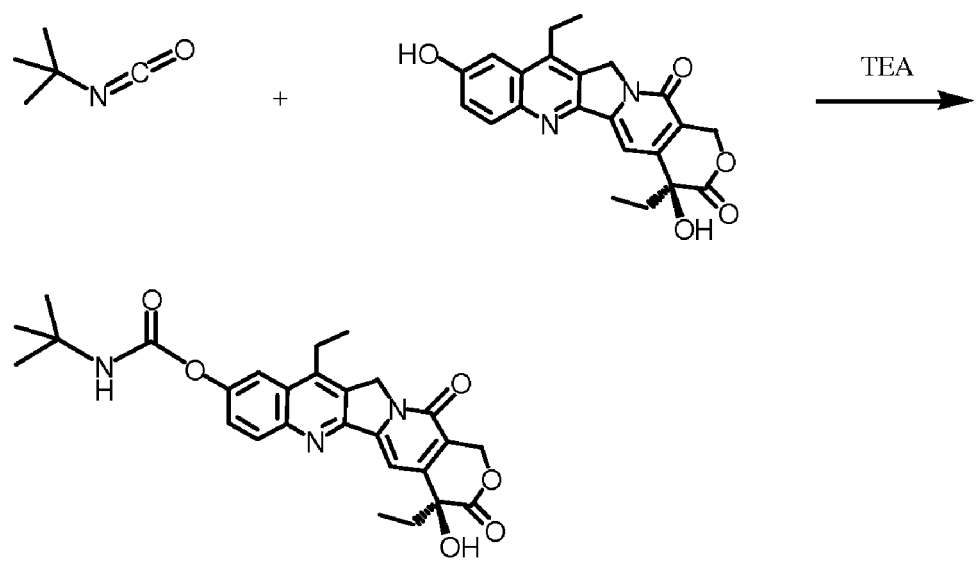
FIG. 14 schematically illustrates the preparation of 10-(N-t-butyl carbamate)-7-ethylcamptothecin.

FIG. 14 illustrates the preparation of 10-(N-t-butyl carbamate)-7-ethylcamptothecin. As used herein, 10-(N-t-butyl carbamate)-7-ethylcamptothecin refers to t-butyl-carbamic acid, (4S)-4,11-diethyl-3,4,12,14-tetrahydro-4-hydroxy-3,14-dioxo-1H-pyrano[3',4':6,7]indolizino[1,2-b]quinolin-9-yl ester. The preparation of 10-(N-t-butyl carbamate)-7-ethylcamptothecin is described in Example 12.

Figure 15:
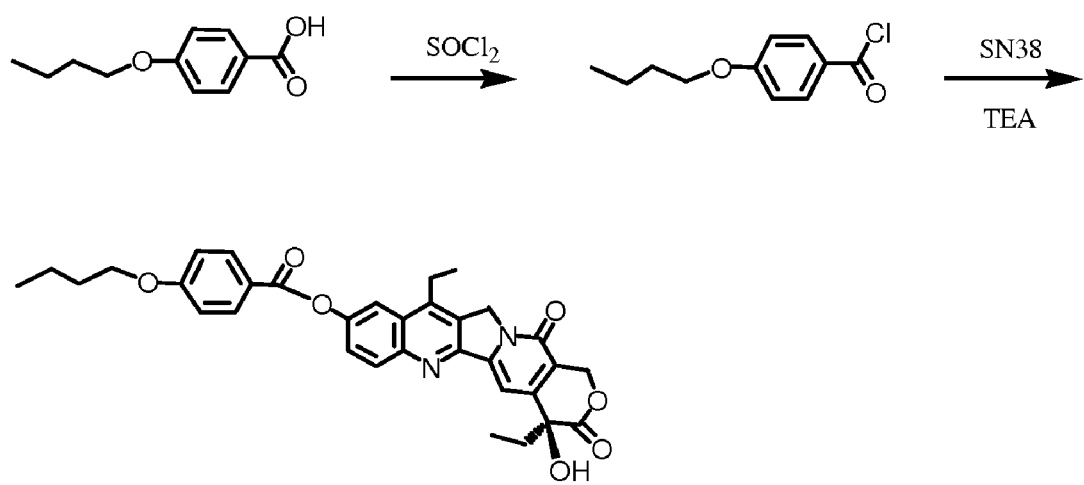
FIG. 15 schematically illustrates the preparation of 10-(4-butoxybenzoyloxy)-7-ethylcamptothecin.

FIG. 15 illustrates the preparation of 10-(4-butoxybenzoyloxy)-7-ethylcamptothecin. As used herein, 10-(4-butoxybenzoyloxy)-7-ethylcamptothecin refers to 4-butoxybenzoic acid, (4S)-4,11-diethyl-3,4,12,14-tetrahydro-4-hydroxy-3,14-dioxo-1H-pyrano[3',4':6,7]indolizino[1,2-b]quinolin-9-yl ester. 4-Butoxybenzoic acid reacts with thionyl chloride to generate 4-butoxybenzoyl chloride which is then coupled with 7-ethyl-10-hydroxycamptothecin to form the 10-(4-butoxybenzoyloxy)-7-ethylcamptothecin. The preparation of 10-(4-butoxybenzoyloxy)-7-ethylcamptothecin is described in Example 13.

Figure 16:
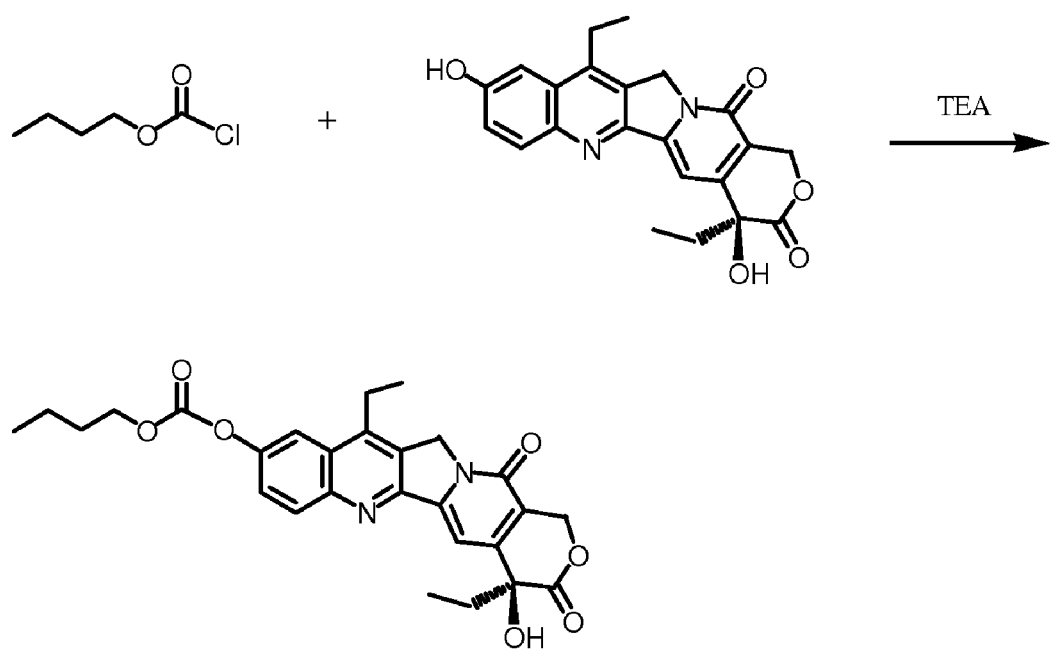
FIG. 16 schematically illustrates the preparation of 10-(n-butyl carbonoyloxy)-7-ethylcamptothecin.

FIG. 16 illustrates the preparation of 10-(n-butyl carbonoyloxy)-7-ethylcamptothecin. As used herein, 10-(n-butyl carbonoyloxy)-7-ethylcamptothecin refers to carbonic acid, n-butyl (4S)-4,11-diethyl-3,4,12,14-tetrahydro-4-hydroxy-3,14-dioxo-1H-pyrano[3',4':6,7]indolizino[1,2-b]quinolin-9-yl ester. n-Butyl chloroformate reacts with 7-ethyl-10-hydroxycamptothecin in the presence of triethylamine to form 10-(n-butyl carbonoyloxy)-7-ethylcamptothecin. The preparation of 10-(n-butyl carbonoyloxy)-7-ethylcamptothecin is described in Example 14.

Figure 17:
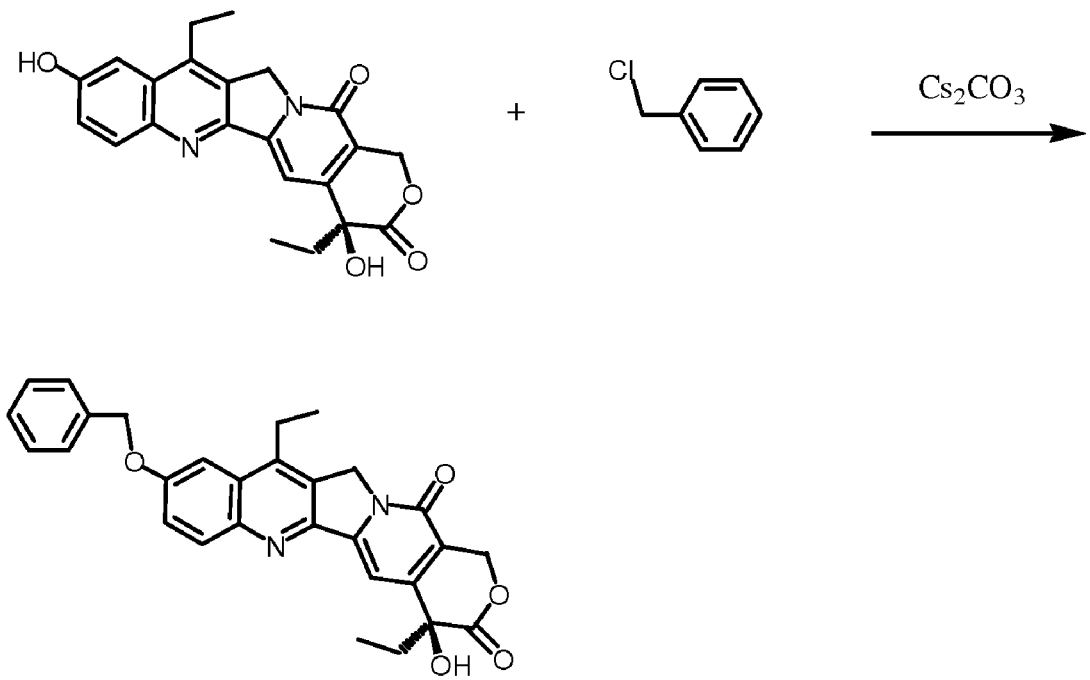
FIG. 17 schematically illustrates the preparation of 10-benzyloxy-7-ethylcamptothecin.

FIG. 17 illustrates the preparation of 10-benzyloxy-7-ethylcamptothecin. As used herein, 10-benzyloxy-7-ethylcamptothecin refers to benzyl (4S)-4,11-diethyl-3,4,12,14-tetrahydro-4-hydroxy-3,14-dioxo-1H-pyrano[3',4':6,7]indolizino[1,2-b]quinolin-9-yl ether. Benzyl chloride reacts with 7-ethyl-10-hydroxycamptothecin in the presence of cesium carbonate to form 10-benzyloxy-7-ethylcamptothecin. The preparation of 10-benzyloxy-7-ethylcamptothecin is described in Example 15.

In another aspect, the present invention provides compositions that include the compounds of the invention. The compositions include one or more compounds of the invention, optionally one or more additional therapeutic agents, and a lipophilic medium. In one embodiment, a lipophilic anticancer drug compound is dissolved in the lipophilic medium. The lipophilic medium (or carrier) of the composition can be any one of a variety of lipophilic mediums including, for example, oils. In one embodiment, the lipophilic medium includes a tocopherol or a tocotrienol. Representative oils useful as the lipophilic medium include the following:

fatty acids and esters thereof, including carboxylic acids of various chain lengths, mostly straight chain, but which could be branched, examples of which include capric, caprylic, caproic, lauric, myristic, stearic, oleic, linoleic, behenic, and as well as saturated or unsaturated fatty acids and esters;

fatty acids esterified with glycerin to form mono-, di-, or triglycerides, which can be synthetic or derived from natural sources, including, but not limited to, for example, glycerides such as soybean oil, cottonseed oil, rapeseed oil, fish oil, castor oil, Capmul MCM, Captex 300, Miglyol 812, glyceryl monooleate, triacetin, acetylated monoglyceride, tristearin, glyceryl behenate, and diacetyl tartaric acid esters of monoglycerides;

glycerides conjugated to other moieties, such as polyethylene glycol (for example, Labrasol, Labrafac, Cremophor EL);

phospholipids, either natural or synthetic, such as dimyristyl phosphatidylcholine, egg lecithin, and pegylated phospholipids;

other fatty esters including myristyl myristate, isopropyl palmitate, sorbitan monooleate, SPAN 80, Tween 80, and sucrose laurate;

fatty alcohols such as stearyl alcohol, lauryl alcohol, benzyl alcohol, or esters or ethers thereof, such as benzyl benzoate; and fat-soluble vitamins and derivatives, for example, vitamin E (including all of the tocopherols and tocotrienols, and tocopherol and tocotrienol derivatives, such as vitamin E succinate, vitamin E acetate, and vitamin E succinate polyethylene glycol (TPGS)).

Organic co-solvents can also be used in the compositions, optionally in combination with water, including for example, ethanol, polyethylene glycol, propylene glycol, glycerol, N-methyl pyrrolidone, and dimethyl sulfoxide.

In a further aspect, the invention provides emulsion, microemulsion, and micelle formulations that include a compound of the invention. Methods for making the emulsions, microemulsions, and micelle formulations are also provided. As used herein, the term "emulsion" refers to a colloidal dispersion of two immiscible liquids, such as an oil and water, in the form of droplets, whose diameter, in general, are between 0.1 and 3.0 microns and that is typically optically opaque, unless the dispersed and continuous phases are refractive index matched. Such systems possess a finite stability, generally defined by the application or relevant reference system, which may be enhanced by the addition of amphiphilic molecules or viscosity enhancers.

The term "microemulsion" refers to a thermodynamically stable isotropically clear dispersion of two immiscible liquids, such as an oil and water, stabilized by an interfacial film of surfactant molecules. A microemulsion has a mean droplet diameter of less than 200 nm, in general between 10-50 nm.

The emulsion and microemulsion formulations include an oil phase and an aqueous phase. The emulsion or microemulsion can be an oil-in-water emulsion or a water-in-oil emulsion.

In the absence of water, mixtures of oil(s) and non-ionic surfactant(s) form clear and isotropic solutions that are known as self-emulsifying drug delivery systems (SEDDS) and can be used to improve lipophilic drug dissolution and oral absorption.

In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.5 weight percent based on the total weight of the formulation.

In one embodiment, the lipophilic medium is present in the formulation in an amount from about 2 to about 20 weight percent based on the total weight of the formulation. In one embodiment, the lipophilic medium is present in the formulation in an amount from about 4 to about 12 weight percent based on the total weight of the formulation. In one embodiment, the lipophilic medium is present in the formulation in an amount from about 6 to about 10 weight percent based on the total weight of the formulation.

In one embodiment of the emulsion or microemulsion, the lipophilic medium includes a tocopherol, and the aqueous medium is water.

In addition to the compounds of the invention, the emulsion or microemulsion formulations can include other components commonly used in emulsions and microemulsions, and, in particular, components that are used in pharmaceutical emulsions and microemulsions. These components include, for example, surfactants and co-solvents. Representative surfactants include nonionic surfactants such as surface active tocopherol derivatives and surface active polymers.

Suitable surface active tocopherol derivatives include tocopherol polyethylene glycol derivatives, such as vitamin E succinate polyethylene glycol (e.g., d-α-tocopherol polyethylene glycol 1000 succinate, TPGS), which is a vitamin E derivative in which a polyethylene glycol is attached by a succinic acid ester at the hydroxyl of vitamin E. The tocopherol polyethylene glycol derivative includes a polyethylene glycol. Suitable tocopherol polyethylene glycol derivatives include polyethylene glycol having a variety of molecular weights (e.g., 200, 300, 400, 600, 1000, or more). As used herein, "vitamin E succinate polyethylene glycol" includes vitamin E succinate polyethylene glycol and derivatives of vitamin E polyethylene glycol having various ester and ether links. TPGS is a non-ionic surfactant (HLB=16-18). Surface active tocopherol derivatives (e.g., TPGS) can be present in the formulations of the invention in an amount from about 1 to about 10 weight percent, about 2 to about 6 weight percent, or about 5 weight percent, based on the total weight of the formulation.

Suitable nonionic surfactants include block copolymers of ethylene oxide and propylene oxide known as POLOXAMERS or PLURONICS. These synthetic block copolymers of having the general structure: $H(OCH_2CH_2)_a(OC_3H_6)_b(OCH_2CH_2)_aOH$. The following variants based on the values of a and b are commercially available from BASF Performance Chemicals (Parsippany, N.J.) under the trade name PLURONIC and consist of the group of surfactants designated by the CTFA name of POLOXAMER 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403. For the most commonly used POLOXAMERS 124, 188, 237, 338, and 407 the values of a and b are 12/20, 79/28, 64/37, 141/44 and 101/56, respectively. In one embodiment the nonionic surfactant is present in the formulation in an amount from about 0.5 to about 5 weight percent based on the total weight of the formulation.

Co-solvents useful in the formulations include ethanol, polyethylene glycol, propylene glycol, glycerol, N-methylpyrrolidone, and dimethylsulfoxide, among others. Polyethylene glycol (PEG) is a hydrophilic, polymerized form of ethylene glycol, consisting of repeating units having the chemical structure: ($-CH_2CH_2O-$). The general formula for polyethylene glycol is $H(OCH_2CH_2)_nOH$. The molecular weight ranges from 200 to 10,000. Such various forms are described by their molecular weights, for example, PEG-200, PEG-300, PEG-400, and the like.

In a further aspect, the invention provides micelle formulations that include a compound of the invention, one or more surfactants, one or more solvents, and an aqueous phase. Micelles are organized aggregates of one or more surfactants in solution. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.0 weight percent based on the total weight of the formulation. Suitable surfactants include those noted above, and in the amounts noted above. In one embodiment of the micelle formulation, the surfactant is tocopherol polyethylene glycol succinate (TPGS).

The micelle formulation can also include additional components such as solvents and co-solvents, including those noted above. In one embodiment, the micelle formulation includes a polyethylene glycol and a lower alkyl alcohol (e.g., ethanol). In one embodiment, the solvents and co-solvents are present in an amount from about 2 to about 20 weight percent based on the total weight of the formulation. The micelle, emulsion, and microemulsion formulations include an aqueous phase. In one embodiment, the aqueous phase includes deionized water. In another embodiment, the aqueous phase includes saline. In another embodiment, the aqueous phase is saline buffered with an organic acid (e.g., succinate, citrate).

The invention also provides the use of the compounds of the invention in the manufacture of a medicament. For example, for compounds of the invention that include a anticancer drug moiety derived from a anticancer drug compound effective in treating cell proliferative disease, the invention provides the use of such compounds in the manufacture of a medicament for the treatment of cell proliferative disease.

In other aspects, methods for administering a compound of the invention to a subject in need thereof, and methods for treating a condition treatable by administration of a therapeutically effective amount of a compound of the invention are also provided. These methods include the administration of the compounds, compositions, emulsion formulations, microemulsion formulations, and micelle formulations described herein.

In one embodiment, the invention provides a method for treating a condition that is treatable by the parent, unmodified anticancer drug compound (e.g., a cell proliferative disease such as cancer). In the method, a therapeutically effective amount of a compound of the invention is administered to a subject in need thereof.

In one embodiment, the invention provides a method for treating a cell proliferative disease by administering a compound of the invention having a anticancer drug moiety derived from a anticancer drug effective in treating cell proliferative disease. Representative cell proliferative diseases treatable by the compounds of the invention include hematologic cancers, such as leukemia, lymphoma, and myeloma; and nonhematologic cancers, such as solid tumor carcinomas (e.g., breast, ovarian, pancreatic, colon, colorectal, non-small cell lung, and bladder), sarcomas, and gliomas.

Therapeutically effective amounts of the compounds will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the compound actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the compounds of the invention can be determined by standard pharmaceutical procedures, in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio $LD_{50}$ to $ED_{50}$. Modified anticancer drug compounds that exhibit large therapeutic indices are particularly suitable in the practice of the methods of the invention. The data obtained from cell culture assays and animal studies may be used in formulating a range of dosage for use in humans or other mammals. The dosage of such compounds lies preferably within a range of circulating concentrations that include the $ED_{50}$ with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The compounds of the invention can be administered alone, or in combination with one or more additional therapeutic agents. For example, in the treatment of cancer, the compounds can be administered in combination with therapeutic agents including, but not limited to, androgen inhibitors, such as flutamide and luprolide; antiestrogens, such as tomoxifen; antimetabolites and cytotoxic agents, such as daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, and idamycin; hormones, such as medroxyprogesterone, estramustine, ethinyl estradiol, estradiol, leuprolide, megestrol, octreotide, diethylstilbestrol, chlorotrianisene, etoposide, podophyllotoxin, and goserelin; nitrogen mustard derivatives, such as melphalan, chlorambucil, methlorethamine, and thiotepa, steroids, such as betamethasone; and other antineoplastic agents, such as live *Mycobacterium bovis*, dicarbazine, asparaginase, leucovorin, mitotane, vincristine, vinblastine, and taxotere. Appropriate amounts in each case will vary with the particular agent, and will be either readily known to those skilled in the art or readily determinable by routine experimentation.

Administration of the compounds of the invention is accomplished by any effective route, for example, parenteral, topical, or oral routes. Methods of administration include inhalational, buccal, intramedullary, intravenous, intranasal, intrarectal, intraocular, intraabdominal, intraarterial, intraarticular, intracapsular, intracervical, intracranial, intraductal, intradural, intralesional, intramuscular, intralumbar, intramural, intraocular, intraoperative, intraparietal, intraperitoneal, intrapleural, intrapulmonary, intraspinal, intrathoracic, intratracheal, intratympanic, intrauterine, intravascular, and intraventricular administration, and other conventional means. The compounds of the invention having anti-tumor activity can be injected directly into a tumor, into the vicinity of a tumor, or into a blood vessel that supplies blood to the tumor.

The emulsion, microemulsion, and micelle formulations of the invention can be nebulized using suitable aerosol propellants that are known in the art for pulmonary delivery of the compounds.

The compounds of the invention may be formulated into a composition that additionally comprises suitable pharmaceutically acceptable carriers, including excipients and other compounds that facilitate administration of the compound to a subject. Further details on techniques for formulation and administration may be found in the latest edition of "Remington's Pharmaceutical Sciences" (Maack Publishing Co., Easton, Pa.).

Compositions for oral administration may be formulated using pharmaceutically acceptable carriers well known in the art, in dosages suitable for oral administration. Such carriers enable the compositions containing the compounds of the invention to be formulated as tablets, pills, dragees, capsules, liquids, gels, syrups, slurries, suspensions, suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins, such as gelatin and collagen. If desired, disintegrating or solubilizing agents may be added, such as the crosslinked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Compounds for oral administration may be formulated, for example, as push-fit capsules made of gelatin, as well as soft, sealed capsules made of gelatin and a coating such as glycerol or sorbitol. Push-fit capsules may contain the compounds mixed with filler or binders such as lactose or starches, lubricants such as talc or magnesium stearate, and, optionally, stabilizers. In soft capsules, the covalent conjugates may be dissolved or suspended in suitable liquids, such as fatty oils, liquid paraffin, or liquid polyethylene glycol with or without stabilizers.

For topical or nasal administration, penetrants appropriate to the particular barrier to be permeated are typically used in the formulation. Examples of these are 2-pyrrolidone, N-methyl-2-pyrrolidone, dimethylacetamide, dimethyl-formamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. For topical administration, the composition may be in the form of a transdermal ointment or patch for systemic delivery of the compound and may be prepared in a conventional manner (see, e.g., Barry, Dermatological Formulations (Drugs and the Pharmaceutical Sciences-Dekker); Harry's Cosmeticology (Leonard Hill Books).

For rectal administration, the compositions may be administered in the form of suppositories or retention enemas. Such compositions may be prepared by mixing the compounds with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration.

Compositions containing the compounds of the invention may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, sustained release, or targeted release, by conventional means (e.g., coating). As noted above, in one embodiment, the compounds are formulated as an emulsion.

After compositions formulated to contain a compound and an acceptable carrier have been prepared, they can be placed in an appropriate container and labeled for use. Thus, in another aspect, the invention provides kits.

Lipophilic anticancer drug compounds of the invention are suitable for administration as oil-in-water emulsions and micelle formulations. The compounds provide for high drug loading to enable small volumes for administration.

Emulsions containing lipophilic anticancer drug compounds of the invention may provide for longer plasma half-life compared to conventional methods of drug compound administration resulting in prolonged exposure of targeted sites to the compounds. Lipophilic anticancer drug compounds may also achieve high permeation through lipoidal membranes of targeted cells. Greater response without an increase in toxicity may be provided by the lipophilic anticancer drug compounds of the invention as compared to unmodified parent compounds.

The following examples are provided to illustrate, not limit, the invention.

EXAMPLES

Example 1

The Preparation of a Representative Lipophilic Anticancer Drug Compound: 10-(benzyl succinate)-7-ethylcamptothecin Preparation of succinic acid monobenzyl ester. A mixture of 5.0 g (0.05 mol) of succinic acid anhydride, 5.4 g (0.05 mol) of benzyl alcohol, 16.25 g (0.05 mol) of cesium carbonate, and 50 ml of N,N-dimethylforamide was stirred at 100° C. for 2 hours. The reaction mixture was cooled to room temperature, and then poured into 200 ml of ethyl acetate. The mixture was washed with saturated aqueous NaCl containing 0.35 N HCl (3×100 mL). The ethyl acetate phase, which contains the product, was collected and dried over anhydrous $MgSO_4$. The $MgSO_4$ was removed via filtration, and the ethyl acetate was removed under reduced pressure. The crude product was purified by crystallization in diethyl ether and hexane to provide 7.34 g of succinic acid monobenzyl ester, 70.47%.

Preparation of 10-(benzyl succinate)-7-ethylcamptothecin. A mixture of 175 mg (0.84 mmol) of succinic acid monobenzyl ester, 92 µL (150 mg, 1.26 mmol) of thionyl chloride, 50 µL of N,N-dimethylformamide and 50 mL of toluene was stirred under nitrogen at room temperature for 4 hours. The toluene and excess thionyl chloride were removed under reduced pressure and the residue was collected. The residue was dissolved in 10 mL of chloroform (Solution A). A mixture of 165 mg (0.42 mmol) of 7-ethyl-10-hydroxycamptothecin (SN38) dissolved in 10 mL of N,N-dimethylacetamide was prepared (Solution B). A mixture of Solution A, Solution B, and 117 µL (85 mg, 0.84 mmol) of triethylamine was stirred under nitrogen at room temperature overnight. The solvents, N,N-dimethylacetamide and chloroform, were removed under reduced pressure. The crude product was purified by column chromatography on silica gel to provide 149 mg of 10-(benzyl succinate)-7-ethylcamptothecin, yield 60.8%. (The silica column was packed with 50/50 ether/hexane, and the eluents were 200 mL of 100% ether, 200 mL of dichloromethane, 400 ml of 1% methanol in dichloromethane, and 200 mL of 4% methanol in dichloromethane).

IR $\nu_{max}$ ($cm^{-1}$): 3256.62, 2937.38, 1740.80, 1657.98, 1609.10, 1556.27, 1511.93, 1455.49, 1414.62, 1355.39, 1303.59, 1259.96, 1228.06, 1213.86, 1163.46, 1133.66, 1106.95, 1076.57, 1054.72, 1030.71, 999.61, 948.39, 918.99, 894.22, 866.33, 836.18, 812.00, 789.65, 748.30, 698.40, 667.37.

MS (Positive ESI): m/z 583.3 (M+H)$^+$.

$^1$H NMR (300 MHz, DMSO-d$_6$): δ 8.269-8.239 (d, J=9.0 Hz, 1H), 8.029-8.021 (d, J=2.4 Hz, 1H), 7.632-7.593 (dd, J=9.3 & 2.4 Hz, 1H), 7.504-7.368 (m, 6H), 6.595 (s, 1H), 5.500 (s, 2H), 5.383 (s, 2H), 5.223 (s, 2H), 3.258-3.183 (q, J=7.5, 2H), 3.062-2.999 (m, 2H), 2.903-2.841 (m, 2H), 1.977-1.890 (m, 2H), 1.365-1.315 (t, J=7.5 Hz, 3H), 0.967-0.919 (t, J=7.2 Hz, 3H).

Example 2

The Preparation of a Representative Lipophilic Anticancer Drug Compound: 20-(benzyl succinate)camptothecin A mixture containing 0.208 g (1 mmol) of succinic acid monobenzyl ester (prepared as in Example 1), 0.348 g (1 mmol) of camptothecin, 0.292 g (2.4 mmol) of 4-(dimethylamino)pyridine, 0.305 g (1.2 mmol) of 2-chloro-1-methylpyridinium iodide, and 25 mL of N,N-dimethylacetamide was stirred at room temperature for 24 hours. After the reaction was completed, the mixture was concentrated to 10 mL. The crude product was purified by column chromatography on silica gel (chloroform-methanol) to provide 259 mg of 20-(benzyl succinate)camptothecin (48.14%).

IR ν$_{max}$ (cm$^{-1}$): 2935.94, 1749.15, 1726.74, 1666.99, 1622.28, 1560.61, 1498.52, 1456.69, 1443.84, 1404.36, 1389.14, 1372.88, 1350.71, 1333.75, 1296.39, 1244.69, 1231.92, 1221.17, 1199.35, 1146.52, 1124.99, 1087.58, 1060.91, 1046.58, 990.16, 977.76, 949.43, 939.09, 925.48, 878.99, 834.14, 819.20, 787.36, 762.33, 721.53, 707.49.

MS (Positive ESI): m/z 539.3 (M+H)$^+$.

$^1$H NMR (300 MHz, CDCl$_3$): δ 8.361 (s, 1H), 8.220-8.191 (d, J=8.7 Hz, 1H), 7.943-7.916 (d, J=8.1 Hz, 1H), 7.841-7.785 (m, 1H), 7.687-7.633 (m, 1H), 7.272-7.172 (m, 6H), 5.721-5.664 (d, J=17.1 Hz, 1H), 5.427-5.370 (d, J=17.1 Hz, 1H), 5.246-5.227 (q, 2H), 5.168-5.053 (q, 2H), 2.964-2.649 (m, 4H), 2.329-2.071 (m, 2H), 1.004-0.954 (t, J=7.5 Hz, 3H).

Example 3

The Preparation of a Representative Lipophilic Anticancer Drug Compound: 10-(benzyl 3,3-tetramethyleneglutarate)-7-ethylcamptothecin Preparation of 3,3-tetramethyleneglutaric acid monobenzyl ester. A mixture of 2.94 g (0.01 mol) of 3,3-tetramethylene glutaric anhydride, 1.08 g (0.05 mol) of benzyl alcohol, 3.25 g (0.01 mol) of cesium carbonate, and 20 mL of N,N-dimethylformamide was stirred at room temperature for 4 hours. The mixture was then poured into 100 mL of ethyl acetate. The mixture was washed with aqueous NaCl containing 0.1 N HCl (3×100 mL). The ethyl acetate phase, which contains the product, was collected and dried over anhydrous MgSO$_4$. The MgSO$_4$ was removed via filtration and the ethyl acetate was removed under reduced pressure. The crude product was purified by column chromatography on silica gel (diethyl ether and hexane) to provide 2.80 g of 3,3-tetramethyleneglutaric acid monobenzyl ester (70%).

Preparation of 10-(benzyl 3,3-tetramethyleneglutarate)-7-ethylcamptothecin. A mixture of 552 mg (2 mmol) of 3,3-tetramethylene glutaric acid monobenzyl ester (prepared as above), 476 mg (4 mmol) of thionyl chloride, 100 μL of N,N-dimethylformamide and 50 mL of toluene was stirred under nitrogen at room temperature overnight. The toluene and excess thionyl chloride were removed under reduced pressure and the residue was collected. The residue was dissolved in 5 mL of chloroform (Solution A). A mixture of 392 mg (1 mmol) of SN38 dissolved in 25 ml of dry N,N-dimethylacetamide was prepared (Solution B). The mixture of Solution A, Solution B, and 202 mg (2 mmol) of triethylamine was stirred under nitrogen at room temperature overnight. The solvents, N,N-dimethylacetamide and chloroform, were removed under reduced pressure. The crude product was purified by column chromatography on silica gel (chloroform-methanol) to provide 340 mg of 10-(benzyl 3,3-tetramethyleneglutarate)-7-ethylcamptothecin (52.3%).

IR ν$_{max}$ (cm$^{-1}$): 3279.2, 2941.40, 2875.20, 1747.75, 1658.46, 1608.05, 1557.44, 1511.13, 1454.51, 1411.85, 1355.96, 1301.47, 1256.79, 1224.39, 1178.66, 1159.36, 1129.46, 1053.72, 1031.22, 976.64, 915.88, 865.98, 837.09, 809.21, 789.73, 738.93, 724.44, 696.82, 671.02.

MS (Positive ESI): m/z 651.5 (M+H)$^+$.

$^1$H NMR (300 MHz, DMSO-d$_6$): δ 8.221-8.191 (d, J=9.0 Hz, 1H), 7.799-7.791 (s, 1H), 7.656 (s, 1H), 7.500-7.462 (dd, J=9.0 & 2.4, 1H), 7.368-7.312 (m, 5H), 5.787-5.285 (q, J=134.1 & 16.5 Hz, 2H), 5.243 (s, 2H), 5.148 (s, 2H), 3.802 (s, 1H), 3.171-3.095 (q, J=7.5 Hz, 2H), 2.899 (s, 2H), 2.716 (s, 2H), 1.974-1.828 (m, 2H), 1.746 (s, 8H), 1.410-1.359 (t, J=7.5 Hz, 3H), 1.066-1.017 (t, J=7.2 Hz, 3H).

Example 4

The Preparation of a Representative Lipophilic Anticancer Drug Compound: 20-(benzyl 3,3-tetramethyleneglutarate)camptothecin A mixture of 552 mg (2 mmol) of 3,3-tetramethylene glutaric acid monobenzyl ester (prepared as in Example 9), 0.348 g (1 mmol) of camptothecin, 0.244 g (2 mmol) of 4-(N,N-dimethylamino)pyridine, 0.255 g (1 mmol) of 2-chloro-1-methylpyridinium iodide, and 30 mL of N,N-dimethylformamide was stirred under nitrogen at room temperature overnight. The mixture was filtered and 100 mL of ethyl acetate was added to the filtrate. The mixture was washed by saturated aqueous NaCl (3×100 mL). The ethyl acetate phase, which contains the product, was collected and dried over anhydrous MgSO$_4$. The MgSO$_4$ was removed via filtration, and the ethyl acetate was removed under reduced pressure. The crude product was purified by column chromatography on silica gel (chloroform-methanol) to provide 295 mg of 20-(benzyl 3,3-tetramethyleneglutarate)camptothecin (48.62%).

IR ν$_{max}$ (cm$^{-1}$): 3065.84, 2956.46, 2869.03, 1726.27, 1672.65, 1628.07, 1565.50, 1497.75, 1456.07, 1405.99, 1382.84 1352.56, 1323.13, 1289.20, 1249.65, 1232.06, 1164.59, 1147.21, 1131.53, 1081.87, 1045.08, 989.39, 979.24, 948.09, 929.22, 909.64, 889.14, 827.65, 811.81, 785.35, 760.72, 751.78, 735.82, 721.86, 698.68, 656.73.

MS (Positive ESI): m/z 607.2 (M+H)$^+$.

$^1$H NMR (300 MHZ, CDCL$_3$): Δ8.373 (S, 1H), 8.228-8.200 (D, J=8.4 HZ, 1H), 7.947-7.920 (D, J=8.1 HZ, 1H), 7.848-7.793 (DT, J$_1$=6.9 HZ, J$_2$=0.9 HZ, 1H), 7.689-7.640 (T, J=7.5 HZ, 1H), 7.323-7.252 (M, 6H), 5.711-5.366 (Q, J$_1$=86.4 HZ, J$_2$=17.1 HZ, 2H), 5.269 (S, 2H), 5.192-5.088 (Q, J$_1$=18.9 HZ, J$_2$=12.3 HZ, 2H), 2.835-2.655 (Q, J$_1$=39.0 HZ, J$_2$=14.7 HZ, 2H), 2.677-2.558 (Q, J$_1$=20.1 HZ, J$_2$=15.6 HZ, 2H), 2.235-2.010 (M, 2H), 1.662-1.601 (M, 8H), 0.960-0.910 (T, J=7.5 HZ, 3H).

Example 5

The Preparation of a Representative Lipophilic Anticancer Drug Compound: 10-(4-methylbenzyl succinate)-7-ethylcamptothecin Preparation of succinic acid mono-(4-methylbenzyl) ester. A mixture of 2.44 g (0.02 mol) of 4-methylbenzyl alcohol, 2.00 g (0.02 mol) of succinic acid anhydride, 6.50 g (0.02 mol) of cesium carbonate, and 150 mL of dioxane was stirred at reflux temperature for 4 hours. The mixture was cooled to room temperature and filtered to remove the solid portion. The solvent was removed under reduced pressure. The crude product was purified by column chromatography on silica gel (ethyl acetate-hexane) to provide 4.022 g of succinic acid mono-(4-methylbenzyl) ester (90.58%).

Preparation of 10-(4-methylbenzyl succinate)-7-ethylcamptothecin. A mixture of 2.22 mg (1 mmol) of succinic acid mono-(4-methylbenzyl) ester, 238 mg (2 mmol) of thionyl chloride, 50 μL of N,N-dimethylformamide and 50 mL of toluene was stirred under nitrogen at room temperature overnight. The toluene and excess thionyl chloride were removed under reduced pressure. To the residue were added 196 mg (0.5 mmol) of SN38 and 100 mL of chloroform. The mixture was stirred for 15 minutes, and then 101 mg (139 μL, 1 mmol) of triethylamine was added into the mixture. The mixture was stirred at refluxed temperature overnight. The crude product was purified by column chromatography on silica gel (chloroform-methanol) to provide 161.5 mg of 10-(4-methylbenzyl succinate)-7-ethylcamptothecin (54.14%).

IR $v_{max}$ (cm$^{-1}$): 3254.86, 3093.11, 2969.83, 2931.49, 1734.49, 1657.60, 1609.14, 1555.71, 1511.47, 1454.37, 1412.71, 1375.88, 1353.49, 1302.76, 1260.20, 1225.41, 1179.96, 1161.11, 1132.24, 1106.36, 1076.24, 1052.92, 1030.10, 988.32, 947.87, 918.99, 894.09, 865.34, 836.06, 807.98, 754.22, 724.56, 696.95, 664.35.

MS (Positive ESI): m/z 597.0 (M+H)$^+$.

$^1$H NMR (300 MHz, CDCl$_3$): δ 8.242-8.212 (d, J=9.0 Hz, 1H), 7.830-7.822 (d, J=2.4 Hz, 1H), 7.660 (s, 1H), 7.529-7.491 (dd, J$_1$=9.0 Hz, J$_2$=2.4 Hz, 1H), 7.282-7.154 (q, J$_1$=30.6 Hz, J$_2$=7.8 Hz, 4H), 5.789-5.286 (q, J$_1$=134.4 Hz, J$_2$=16.5 Hz, 2H), 5.267 (s, 2H), 5.151 (s, 2H), 3.733 (s, 1H), 3.188-3.111 (q, J=7.8 Hz, 2H), 3.016-2.957 (m, 2H), 2.885-2.824 (m, 2H), 2.346 (s, 3H), 1.971-1.828 (m, 2H), 1.419-1.367 (t, J=7.8 Hz, 3H), 1.0769-1.020 (t, J=7.2 Hz, 3H).

Example 6

The Preparation of a Representative Lipophilic Anticancer Drug Compound: 10-(2,4,6-trimethylbenzyl succinate)-7-ethylcamptothecin Preparation of succinic acid mono-(2,4,6-trimethylbenzyl) ester. A mixture of 1.50 g (0.01 mol) of 2,4,6-trimethylbenzyl alcohol, 1.00 g (0.01 mol) of succinic acid anhydride, 3.25 g (0.01 mol) of cesium carbonate, and 100 ml of dioxane was stirred at reflux temperature for 4 hours. The reaction mixture was cooled to room temperature and then filtered to remove the solid cesium carbonate. The solvent was removed under reduced pressure. The crude product was purified by column chromatography on silica gel (acetone-hexane) to provide 1.167 g of succinic acid mono-(2,4,6-trimethylbenzyl) ester (46.62%).

Preparation of 10-(2,4,6-trimethylbenzyl succinate)-7-ethylcamptothecin. A mixture of 250 mg (1 mmol) of succinic acid mono-(2,4,6-trimethylbenzyl) ester, 238 mg (2 mmol) of thionyl chloride, 50 μL of N,N-dimethylformamide, and 50 mL of toluene was stirred for 4 hours at room temperature. The solvent and excess thionyl chloride were removed under reduced pressure and the residue collected. The residue was dissolved in 5 mL of chloroform (Solution A). A mixture of 196 mg (0.5 mmol) of SN38 dissolved in 20 mL of dry N,N-dimethylacetamide was prepared. The mixture of Solution A, Solution B, and 101 mg (139 μL, 1 mmol) of triethylamine was stirred under nitrogen at room temperature overnight. The solvents, N,N-dimethylacetamide, and chloroform, were removed under reduced pressure. The crude product was purified by column chromatography on silica gel (chloroform/methanol) to provide 84 mg of 10-(2,4,6-trimethylbenzyl succinate)-7-ethylcamptothecin (26.9%).

IR $v_{max}$ (cm$^{-1}$): 3317.84, 3093.22, 2972.35, 1747.29, 1731.81, 1660.68, 1612.15, 1555.76, 1512.72, 1463.15, 1437.01, 1376.42, 1354.49, 1302.28, 1274.09, 1259.28, 1223.69, 1207.50, 1181.03, 1162.60, 1130.19, 1105.70, 1054.94, 1032.68, 997.75, 971.41, 947.24, 919.42, 900.66, 852.32, 813.44, 790.64, 721.70, 697.53, 672.00, 664.59.

MS (Positive ESI): m/z 625.5 (M+H)$^+$.

$^1$H NMR (300 MHz, CDCl$_3$): δ 8.223-8.192 (d, J=9.3 Hz, 1H), 7.821-7.812 (d, J=2.7 Hz, 1H), 7.655 (s, 1H), 7.485-7.447 (dd, J$_1$=9.0 Hz, J$_2$=2.4 Hz, 1H), 6.888 (s, 2H), 5.785-5.285 (t, J=133.7 & 16.2 Hz, 2H), 5.263 (s, 2H), 5.250 (s, 2H), 3.830 (s, 1H), 3.191-3.115 (q, J=7.8 Hz, 2H), 3.007-2.963 (m, 2H), 2.831-2.808 (m, 2H), 2.353 (s, 6H), 2.280 (s, 3H), 1.974-1.832 (m, J=7.5 Hz, 2H), 1.425-1.374 (t, J=7.5 Hz, 3H), 1.066-1.017 (t, J=7.2 Hz, 3H).

Example 7

The Preparation of a Representative Lipophilic Anticancer Drug Compound: 10-(2,3,4,5,6-pentamethylbenzyl succinate)-7-ethylcamptothecin Preparation of succinic acid mono-(2,3,4,5,6-pentamethylbenzyl) ester. A mixture containing 1.78 g (0.01 mol) of 2,3,4,5,6-trimethylbenzyl alcohol, 1.00 g (0.01 mol) of succinic acid anhydride, 100 mg (0.01 mol) of tin (II) 2-ethylhexanoate, and 100 mL of xylene was stirred at reflux temperature for 4 hours. The solvent was removed under reduced pressure. The crude product was purified by column chromatography on silica gel (acetone/hexane) to provide 2.12 g of succinic acid mono-(2,3,4,5,6-pentamethylbenzyl) ester (76.3%).

Preparation of 10-(2,3,4,5,6-pentamethylbenzyl succinate)-7-ethylcamptothecin. A mixture of 154 mg (0.55 mmol) of succinic acid mono-(2,3,4,5,6-pentamethylbenzyl) ester, 119 mg (1 mmol) of thionyl chloride, 50 μL of N,N-dimethylformamide, and 50 mL of toluene was stirred 4 hours at room temperature. The solvent and excess thionyl chloride were removed under reduced pressure and the residue was collected. The residue was dissolved in 5 mL of chloroform (Solution A). A mixture of 196 mg (0.5 mmol) of SN38 dissolved in 20 mL of dry N,N-dimethylacetamide was prepared (Solution B). A mixture of Solution A, Solution B, and 56 mg (77 μL, 1 mmol) of triethylamine was stirred under nitrogen at room temperature overnight. The solvents, N,N-dimethylacetamide and chloroform, were removed under reduced pressure. The crude product was purified by column chromatography on silica gel (chloroform-methanol) to provide 180.8 mg of 10-(2,3,4,5,6-pentamethylbenzyl succinate)-7-ethylcamptothecin (55.40%).

IR $v_{max}$ (cm$^{-1}$): 3453.81, 3023.58, 2969.52, 2936.33, 1763.01, 1738.80, 1708.71, 1663.29, 1611.21, 1558.82, 1508.40, 1453.26, 1429.42, 1375.78, 1350.65, 1318.22, 1225.31, 1205.41, 1181.41, 1152.46, 1135.77, 1070.32, 1054.56, 1032.88, 979.85, 939.40, 914.43, 875.20, 850.86, 835.29, 822.96, 804.10, 753.60, 725.15, 698.69, 668.10.

MS (Positive ESI): m/z 653.3 (M+H)$^+$.

$^1$H NMR (300 MHz, CDCl$_3$): δ 8.222-8.192 (d, J=9.0 Hz, 1H), 7.832-7.824 (d, J=2.4 Hz, 1H), 7.654 (s, 1H), 7.498-7.459 (dd, J$_1$=9.0 Hz, J$_2$=2.4 Hz, 1H), 5.790-5.288 (q, J$_1$=135.3 Hz, J$_2$=16.5 Hz, 2H), 5.339 (s, 2H), 5.267 (s, 2H), 3.735 (s, 1H), 3.193-3.118 (q, J=7.5 Hz, 2H), 3.010-2.957 (m, 2H), 2.885-2.793 (m, 2H), 2.347 (s, 6H), 2.254 (s, 3H), 2.227 (s, 6H), 1.948-1.853 (m, 2H), 1.424-1.374 (t, J=7.5 Hz, 3H), 1.071-1.022 (t, J=7.5 Hz, 3H).

Example 8

The Preparation of a Representative Lipophilic Anticancer Drug Compound: 10-(1-octyl succinate)-7-ethylcamptothecin Preparation of succinic acid mono-(1-octyl) ester. A mixture containing 4.1 g (31.5 mmol) of 1-octanol, 100 mg of tin(II) 2-ethylhexanoate and 3.0 g (30 mmol) of succinate anhydride was stirred under nitrogen at 140° C. for 2 hours. The mixture was cooled to room temperature and, the crude product was purified by column chromatography on silica gel (40% ethyl acetate in hexane) to provide 3.134 g of succinic acid mono-(1-octyl) ester (45.36%).

Preparation of 10-(1-octyl succinate)-7-ethylcamptothecin. A mixture containing 0.461 g (2 mmol) of succinic acid mono-(1-octyl) ester, 0.357 g (3 mmol) of thionyl chloride, and 50 mL of toluene was stirred at room temperature overnight. The solvent and excess thionyl chloride were removed under reduced pressure. To the residue was added 20 mL of toluene. The solvent was removed under reduced pressure again. The residue was dissolved in 10 mL of dichloromethane (Solution A). A mixture of 0.392 g (1 mmol) of SN38 dissolved in 25 mL of dry N,N-dimethylacetamide was prepared (Solution B). A mixture of Solution A, Solution B and 0.222 g (2.2 mmol, 306 µL) of triethylamine was stirred overnight. After the reaction was completed, 100 mL of ethyl acetate was added into the mixture. The mixture was washed with saturated aqueous NaCl (3×100 mL). The ethyl acetate phase, which contains the product, was collected and dried over anhydrous MgSO$_4$. The MgSO$_4$ was removed via filtration, and then the ethyl acetate was removed under reduced pressure. The crude product was purified by column chromatography on silica gel (chloroform/methanol) to provide 0.448 g of 10-(1-octyl succinate)-7-ethylcamptothecin (74.08%).

IR ν$_{max}$ (cm$^{-1}$): 3245.40, 2928.02, 2855.48, 1761.71, 1736.17, 1660.96, 1596.76, 1507.87, 1467.21, 1412.68, 1357.58, 1317.97, 1281.77, 1258.39, 1226.72, 1211.52, 1164.23, 1129.65, 1107.04, 1063.66, 1038.99, 1011.86, 973.23, 918.87, 895.14, 866.83, 849.81, 829.97, 808.84, 758.60, 739.37, 722.82, 664.02.

MS (Positive ESI): m/z 605.3 (M+H)$^+$.

$^1$H NMR (300 MHz, CDCl$_3$): δ 8.251-8.220 (d, J=9.3 Hz, 1H), 7.844-7.836 (d, J=2.4 Hz, 1H), 7.654 (s, 1H), 7.592-7.554 (dd, J=9.0 & 2.1 Hz, 1H), 5.785-5.285 (t, J=133.8 & 16.2 Hz, 2H), 5.265 (s, 2H), 4.170 (t, J=6.9 Hz, 2H), 3.819 (s, 1H), 3.196-3.119 (q, J=7.8, 2H), 3.011-2.968 (t, J=6.5 Hz, 2H), 2.831-2.808 (t, J=6.6 Hz, 2H), 1.972-1.807 (m, J=6.9 Hz, 2H), 1.704-1.612 (m, J=6.9 Hz, 2H), 1.427-1.376 (t, J=7.5 Hz, 3H), 1.376-1.263 (m, 10H), 1.066-1.017 (t, J=7.2 Hz, 3H), 0.880-0.845 (t, J=6.9 Hz, 3H).

Anal. Calcd. for C$_{34}$H$_{40}$N$_2$O$_8$: C, 67.53; H, 6.67; N, 4.63. Found: C, 67.42; H, 6.74; N, 4.44.

Example 9

The Preparation of a Representative Lipophilic Anticancer Drug Compound: 20-(1-octyl succinate)camptothecin A mixture of 0.276 g of succinic acid mono-(1-octanyl) ester (prepared as in Example 5), 0.348 g of camptothecin, 0.292 g of 4-(dimethylamino)pyridine, 0.305 g of 2-chloro-1-methylpyridinium iodide, and 25 mL of N,N-dimethylacetamide was stirred at room temperature for 24 hours. After the reaction was completed, 100 mL of ethyl acetate was added to the reaction mixture. The mixture was washed with saturated aqueous NaCl (3×100 mL). The ethyl acetate phase, which contains the product, was collected and dried over anhydrous MgSO$_4$. The MgSO$_4$ was removed via filtration, and the ethyl acetate was removed under reduced pressure. The crude product was purified by column chromatography on silica gel (50% ethyl acetate in hexane) to provide 0.4275 g of 20-(1-octyl succinate)camptothecin (76.25%).

IR ν$_{max}$ (cm$^{-1}$): 2927.98, 2855.69, 1754.78, 1745.76, 1728.05, 1673.12, 1644.69, 1626.51, 1560.00, 1499.99, 1457.76, 1425.73, 1404.64, 1364.85, 1351.26, 1316.57, 1247.29, 1229.45, 1218.09, 1169.49, 1146.00, 1127.49, 1087.51, 1061.25, 1042.03, 988.08, 964.78, 945.18, 927.63, 908.47, 889.93, 822.94, 813.15, 786.37, 761.38, 722.55, 706.04, 674.58.

MS (Positive ESI): m/z 561.3 (M+H)$^+$.

$^1$H NMR (300 MHz, CDCl$_3$): δ 8.393 (s, 1H), 8.244-8.216 (d, J=8.4 Hz, 1H), 7.954-7.928 (d, J=7.8 Hz, 1H), 7.860-7.804 (dt, J=6.9 & 1.2 Hz, 1H), 7.694-7.646 (t, J=7.2 Hz, 1H), 7.282 (s, 1H), 5.713-5.368 (t, J=86.25 & 17.4 Hz, 2H), 5.285 (s, 2H), 4.111-3.977 (m, 2H), 2.878-2.819 (s, 2H), 2.667-2.619 (m, 2H), 2.319-2.115 (m, 2H), 1.559-1.515 (t, J=6.6 Hz, 2H), 1.263-1.193 (m, 10H), 1.017-0.967 (m, J=7.5 Hz, 3H), 0.879-0.834 (t, J=7.5 Hz, 3H).

Anal. Calcd. for C$_{32}$H$_{36}$N$_2$O$_7$: C, 68.55; H, 6.47; N, 5.00. Found: C, 68.61; H, 6.51; N, 4.94.

Example 10

The Preparation of a Representative Lipophilic Anticancer Drug Compound: 10-octanoyloxy-7-ethylcamptothecin A mixture of camptothecin (0.348 g, 1 mmol), octanoic acid (0.288 g, 2 mmol), 2-chloro-1-methyl pyridinium (0.255 g, 1 mmol), 4-(dimethylamino)pyridine (0.244 g, 2 mmol), and N,N-dimethylacetamide (30 mL) was stirred at 50° C. overnight. The mixture was cooled to room temperature and then filtered. The filtrate was added into 150 mL of ethyl acetate and washed with saturated aqueous NaCl (3×100 mL). The ethyl acetate phase, which contains the product, was collected and dried over anhydrous MgSO$_4$. The MgSO$_4$ was removed via filtration, and the ethyl acetate was removed under reduced pressure. The crude product was purified by column chromatography on silica gel (25% ethyl acetate in hexane and 25% acetone in hexane) to provide 0.226 g of 10-octanoyloxy-7-ethylcamptothecin (97.4%):

IR ν$_{max}$ (cm$^{-1}$): 2924.13, 2854.44, 1751.78, 1742.77, 1666.55, 1616.71, 1560.03, 1498.57, 1454.34, 1402.98, 1380.22, 1367.01, 1350.18, 1322.18, 1293.20, 1253.58, 1229.81, 1185.43, 1149.31, 1129.03, 1086.17, 1075.28, 1061.95, 1044.18, 988.67, 959.99, 945.77, 927.10, 914.25, 889.39, 851.73, 821.93, 813.06, 786.54, 765.80, 757.53, 722.47, 706.26 671.91.

MS (Positive ESI): m/z 475.4 (M+H)$^+$.

$^1$H NMR (300 MHz, CDCl$_3$): δ 8.399 (s, 1H), 8.233-8.204 (d, J=8.7 Hz, 1H), 7.960-7.933 (d, J=8.1 Hz, 1H), 7.865-7.810 (dt, J=6.9 & 1.2 Hz, 1H), 7.699-7.649 (t, J=7.8 Hz, 1H), 7.222 (s, 1H), 5.711-5.387 (t, J=79.95 & 17.4 Hz, 2H), 5.288 (s, 2H), 2.517-2.457 (m, 2H), 2.361-2.2.097 (m, 2H), 1.699-1.600 (m, 2H), 1.389-1.213 (m, 8H), 1.002-0.952 (m, J=7.5 Hz, 3H), 0.879-0.834 (t, J=6.6 Hz, 3H).

Anal. Calcd. for C$_{28}$H$_{30}$N$_2$O$_5$: C, 70.87; H, 6.37; N, 5.90. Found: C, 70.45; H, 6.35; N, 5.83.

Example 11

The Preparation of a Representative Lipophilic Anticancer Drug Compound: 10-(N-n-butyl carbamate)-7-ethylcamptothecin A mixture containing 392 mg of 7-ethyl-10-hydroxycamptothecin, 50 mL of N,N-dimethylformamide, 300 µL of n-butyl isocyanate, and 100 µL of triethylamine was stirred at room temperature overnight. The solvent was removed under reduced pressure. The crude product was purified by column chromatography on silica gel (chloroform-methanol) to provide 241 mg of 10-(N-n-butyl carbamate)-7-ethylcamptothecin (49.0%).

IR ν$_{max}$ (cm$^{-1}$): 3311.68, 2963.36, 2934.01, 2873.22, 1726.55, 1660.56, 1614.07, 1592.75, 1554.91, 1534.17, 1506.57, 1461.72, 1438.43, 1414.98, 1400.04, 1359.28, 1302.54, 1232.50, 1219.93, 1190.03, 1163.64, 1108.73, 1077.75, 1051.81, 1032.93, 998.53, 949.77, 919.57, 868.78, 837.67, 816.51, 805.42, 789.19, 724.38, 697.33, 669.42.

MS (Positive ESI): m/z 492.5 (M+H)$^+$.

$^1$H NMR (300 MHz, DMSO-d$_6$): δ 8.175-8.144 (d, J=9.3 Hz, 1H), 7.972-7.932 (m, 2H), 7.647-7.608 (dd, J$_1$=9.3 Hz, J$_2$=2.4 Hz, 1H), 6.535 (s, 1H), 5.429 (s, 2H), 5.330 (s, 2H), 3.195-3.076 (m, 4H), 1.902-1.814 (m, 2H), 1.532-1.438 (m, 2H), 1.381-1.252 (m, 5H), 0.929-0.843 (m, 6H).

Example 12

The Preparation of a Representative Lipophilic Anticancer Drug Compound: 10-(N-t-butyl carbamate)-7-ethylcamptothecin A mixture of 392 mg of 7-ethyl-10-hydroxycamptothecin, 50 mL of N,N-dimethylformamide, 122 µL of t-butyl isocyanate, and 50 µL of triethylamine was stirred at room temperature overnight. The solvent was removed under reduced pressure. The crude product was purified by column chromatography on silica gel (chloroform-methanol) to provide 117 mg of 10-(N-t-butyl carbamate)-7-ethylcamptothecin (23.83%).

IR ν$_{max}$ (cm$^{-1}$): 3301.52, 2967.69, 2928.63, 1738.99, 1656.23, 1607.52, 1535.51, 1505.62, 1455.34, 1414.57, 1393.91, 1365.75, 1268.60, 1234.30, 1211.66, 1177.24, 1161.48, 1131.42, 1105.92, 1076.52, 1051.22, 1018.33, 967.45, 921.76, 867.08, 837.99, 822.29, 806.97, 786.89, 742.99, 724.35, 690.61, 670.14.

MS (Positive ESI): m/z 492.5 (M+H)$^+$.

$^1$H NMR (300 MHz, CDCl$_3$): δ 8.216-8.185 (d, J=9.3 Hz, 1H), 7.820-7.812 (d, J=2.4 Hz, 1H), 7.629 (s, 1H), 7.618-7.580 (dd, J$_1$=9.0 Hz, J$_2$=2.4 Hz, 1H), 5.779-5.279 (q, J$_1$=133.8 Hz, J$_2$=16.2 Hz, 2H), 5.229 (s, 2H), 5.172 (s, 1H), 3.845 (s, 1H), 3.181-3.105 (q, J=7.5 Hz, 2H), 1.960-1.824 (m, 2H), 1.447 (s, 9H), 1.421-1.369 (t, J=7.8 Hz, 3H), 1.059-1.010 (t, J=7.2 Hz, 3H).

Example 13

The Preparation of a Representative Lipophilic Anticancer Drug Compound: 10-(4-butoxybenzoyloxy)-7-ethylcamptothecin A mixture of 0.582 g (3 mmol) of 4-butoxybenzoic acid, 0.587 g (5 mmol) thionyl chloride, and 50 mL of toluene was stirred at room temperature for 24 hours. The solvent and excess thionyl chloride were removed under reduced pressure at 50° C. and the residue was collected. The residue was dissolved in 15 mL of dichloromethane (Solution A). A mixture of 0.392 g (1 mmol) of 7-ethyl-10-hydroxycamptothecin was dissolved in 30 mL of N,N-dimethylacetamide (Solution B). The mixture of Solution A, Solution B, and 0.303 g (417 µL) of triethylamine was stirred at room temperature for 24 hours. 100 mL of ethyl acetate was added into the mixture. The mixture was washed with saturated aqueous NaCl (3×100 mL). The ethyl acetate phase, which contains the product, was collected and dried over anhydrous MgSO$_4$. The MgSO$_4$ was removed via filtration, and the ethyl acetate was removed under reduced pressure. The crude product was purified by column chromatography on silica gel (chloroform/methanol) to provide 482 mg of 10-(4-butoxybenzoyloxy)-7-ethylcamptothecin (84.77%).

IR ν$_{max}$ (cm$^{-1}$): 3258.08, 3090.89, 2938.50, 2875.33, 1750.47, 1730.55, 1657.13, 1606.02, 1554.14, 1511.42, 1459.01, 1440.21, 1422.30, 1392.20, 1360.33, 1323.87, 1254.94, 1227.06, 1213.96, 1182.95, 1162.94, 1121.32, 1105.72, 1079.40, 1051.10, 1029.09, 1005.90, 969.77, 949.52, 919.41, 884.74, 871.14, 843.50, 825.47, 814.32, 802.61, 788.38, 760.06, 727.18, 711.11, 689.39, 675.89, 664.17.

MS (Positive ESI): m/z 569.3 (M+H)$^+$.

$^1$H NMR (300 MHZ, CDCL$_3$): δ 8.280-8.250 (s, J=9 Hz, 1H), 8.208-8.179 (d, J=8.7 Hz, 2H), 7.933-7.925 (d, J=2.4 Hz, 1H), 7.686-7.648 (m, 2H), 7.021-6.992 (d, J=8.7 Hz, 2H), 5.774-5.274 (q, J$_1$=133.5 Hz, J$_2$=16.5 Hz, 2H), 5.261 (s, 2H), 4.098-4.055 (t, J=6.3 Hz, 2H), 3.976 (s, 1H), 3.199-3.123 (q, J=7.8 Hz, 2H), 1.975-1.785 (m, 4H), 1.600-1.476 (m, 2H), 1.437-1.387 (t, J=7.5Hz, 3H), 1.063-0.989 (m, 6H).

Example 14

The Preparation of a Representative Lipophilic Anticancer Drug Compound: 10-(n-butyl carbonoyloxy)-7-ethylcamptothecin A mixture of 0.392 g (1 mmol) of 7-ethyl-10-hydroxycamptothecin, 20 mL of N,N-dimethylacetamide, 0.137 g (1 mmol) of n-butyl chloroformate and 0.101 g (1 mmol) of triethylamine was stirred overnight. 200 mL of ethyl acetate was added into the mixture, and the mixture was washed with saturated aqueous NaCl (3×100 mL). The ethyl acetate phase, which contains the product, was collected and dried over anhydrous MgSO$_4$. The MgSO$_4$ was removed via filtration, and the ethyl acetate was removed under reduced pressure. The crude product was purified with column chromatography on silica gel (chloroform-methanol) to provide 351.6 mg of 10-(n-butyl carbonoyloxy)-7-ethylcamptothecin (71.4%).

IR ν$_{max}$ (cm$^{-1}$) 3470.02, 2967.74, 2939.05, 2873.53, 1754.50, 1735.90, 1656.95, 1607.61, 1558.50, 1505.89, 1455.82, 1415.95, 1383.05, 1358.92, 1307.34, 1235.17, 1157.93, 1122.89, 1109.31, 1081.80, 1053.62, 1032.97, 1008.08, 945.70, 915.03, 885.85, 867.02, 839.94, 824.68, 803.20, 779.89, 757.86, 724.93, 705.68, 693.49, 670.43.

MS (Positive ESI): m/z 493.3 (M+H)$^+$.

$^1$H NMR (300 MHz, CDCl$_3$): δ 8.258-8.227 (d, J=9.3 Hz, 1H), 7.920-7.911 (d, J=2.7 Hz, 1H), 7.668-7.629 (dd, J=9.3 & 2.4, 1H), 7.657 (s, 1H), 5.779-5.279 (t, J=133.5 & 16.2 Hz, 2H), 5.258 (s, 2H), 3.177-3.102 (t, J=6.6 Hz, 2H), 3.890 (s, 1H), 3.195-3.119 (t, J=7.5 Hz, 2H), 1.970-1.837 (m, 2H), 1.830-1.742 (m, 2H), 1.565-1.440 (m, 2H), 1.429-1.378 (t, J=7.8 Hz, 3H), 1.061-0.982 (m, 6H).

Anal. Calcd. for C$_{28}$H$_{30}$N$_2$O$_5$: C, 65.84; H, 5.73; N, 55.69. Found: C, 65.59; H, 5.62; N, 5.59.

Example 15

The Preparation of a Representative Lipophilic Anticancer Drug Compound: 10-benzyloxy-7-ethylcamptothecin A mixture of 196 mg (0.5 mmol) of 7-ethyl-10-hydroxy-camptothecin, 126 mg (1 mmol) of benzyl chloride, and 163 mg (0.5 mmol) of cesium carbonate, and 50 mL of dioxane was refluxed for 4 hours. The mixture was cooled to room temperature and then filtered to remove the solid portion. The solvent was removed under reduced pressure. The crude product was then purified by column chromatography on silica gel (chloroform-methanol) to provide 150 mg of 10-benzyloxy-7-ethylcamptothecin (62.2%).

IR ν$_{max}$ (cm$^{-1}$): 3256.81, 3089.77, 2934.72, 2876.62, 1748.37, 1658.36, 1603.20, 1556.65, 1509.64, 1454.85, 1434.53, 1380.88, 1362.42, 1300.98, 1276.30, 1224.23, 1155.78, 1104.29, 1074.14, 1051.10, 1030.02, 1002.86, 947.29, 918.29, 832.67, 754.67, 740.49, 727.08, 699.31, 665.68.

MS (Positive ESI): m/z 483.3 (M+H)$^+$.

$^1$H NMR (200 MHz, CDCl$_3$): δ 8.126-8.116 (d, J=9.2 Hz, 1H), 7.601 (s, 1H), 7.562-7.358 (m, 7H), 5.788-5.706 (d, J=16.4, 1H), 5.334-5.258 (d, J=15.2 Hz, 1H), 5.258 (s, 2H), 5.216 (s, 2H), 3.815 (s, 1H), 3.152-3.039 (q, J=7.4 Hz, 2H), 1.956-1.830 (m, 2H), 1.358-1.281 (t, J=7.6 Hz, 3H), 1.068-0.994 (t, J=7.4 Hz, 3H).

Example 16

In vitro Cytotoxicity of Representative Lipophilic Anticancer Drug Compounds

In this example, the in vitro cytotoxicity, as measured by GI$_{50}$ (50% of growth inhibition) values, was determined for representative lipophilic anticancer drug compounds of the invention. The GI$_{50}$ values of 10-(benzyl succinate)-7-ethyl-camptothecin, 20-(benzyl succinate)camptothecin, 10-(benzyl 3,3-tetramethyleneglutarate)-7-ethylcamptothecin, 10-(4-methylbenzyl succinate)-7-ethylcamptothecin, 10-(2,4,6-trimethylbenzyl succinate)-7-ethylcamptothecin, 10-(2,3,4,5,6-pentamethylbenzyl succinate)-7-ethylcamptothecin, 10-(1-octyl succinate)-7-ethylcamptothecin, 20-(1-octyl succinate)camptothecin, 10-(N-n-butyl carbamate)-7-ethylcamptothecin, 10-(N-t-butyl carbamate)-7-ethylcamptothecin, 10-(4-butoxybenzoyloxy)-7-ethylcamptothecin, 10-(n-butyl carbonoyloxy)-7-ethylcamptothecin, 10-benzyloxy-7-ethylcamptothecin, were compared to the National Cancer Institute (NCI) GI$_{50}$ values for camptothecin, 10-hydroxy-camptothecin, SN38, irinotecan, and topotecan in the following cancer cell lines: H460 (non-small cell lung), HCT-15 (colorectal), HT-116 (colorectal), and SKOV-3 (ovarian).

The study was performed using a solution of the lipophilic anticancer drug compounds in DMSO (1 mM) diluted in the corresponding cell media. The cells were in contact with varying concentrations of the test article for a period of 48 hours. At the end of 48 hours, staining with Sulforhodamine B was performed to determine the number of viable cells and calculate the degree of cellular growth inhibition as compared to a control group. The calculated GI$_{50}$ values are shown in Table 1.

TABLE 1

Concentration of lipophilic anticancer drug compound that produce 50% cell growth inhibition (GI$_{50}$)

| | H460 (NSCLC) | HCT-15 (COLON) | HCT-116 (COLON) | SKOV-3 (OVARIAN) |
|---|---|---|---|---|
| 10-(benzyl succinate)-7-ethylcamptothecin | 0.372 nM | 50.1 nM | 10.7 nM | 1.29 nM |
| 20-(benzyl succinate)camptothecin | 380 nM | 1.3 μM | 630 nM | 562 nM |
| 10-(4-methylbenzyl succinate)-7-ethylcamptothecin | 5.37 nM | 75.43 nM | 2.29 nM | 6.16 nM |
| 10-(2,4,6-trimethylbenzyl succinate)-7-ethylcamptothecin | 5.12 nM | 31.62 nM | 3.54 nM | 3.67 nM |
| 10-(2,3,4,5,6-pentamethylbenzyl succinate)-7-ethylcamptothecin | 3.82 nM | 32.35 nM | 3.09 nM | 2.13 nM |
| 10-(benzyl 3,3-tetramethyleneglutarate)-7-ethylcamptothecin | 8.91 nM | 85.1 nM | 3.49 nM | 2.95 nM |
| 10-(N-n-butyl carbamate)-7-ethylcamptothecin | 1.2 nM | 44.7 nM | 1.1 nM | 0.398 nM |
| 10-(N-t-butyl carbamate)-7-ethylcamptothecin | 5.75 nM | 158 nM | 15.1 nM | 1.29 nM |
| 10-(n-butyl carbonoyloxy)-7-ethylcamptothecin | 2.95 nM | 120 nM | 0.58 nM | 0.275 nM |
| 10-(4-butoxybenzoyloxy)-7-ethylcamptothecin | 28.2 nM | 141 nM | 5.62 nM | 5.5 nM |
| 10-(1-octyl succinate)-7-ethylcamptothecin | 2.46 μM | 661 nM | 9.75 nM | 3.46 nM |
| 20-(1-octyl succinate)camptothecin | 165 nM | 354 nM | 765.5 nM | 2.42 μM |
| 10-benzyloxy-7-ethylcamptothecin | 0.32 nM | 5.66 nM | 4.52 nM | 15 nM |
| Camptothecin (NCI) | 16 Nm | 160 nM | 40 nM | 25 nM |
| 10-hydroxycamptothecin (NCI) | 11 nM | 356 nM | 27 nM | — |
| 7-ethyl-10hydroxycamptothecin (NCI) | 1.4 nM | 7.9 nM | 21 nM | 1 nM |
| Irrinotecan (NCI) | 5.1 μM | 31.6 nM | 7.9 μM | — |
| Topotecan (NCI) | 19.9 nM | 501 nM | 39.8 nM | — |

While illustrative embodiments have been illustrated and described, it will be appreciated that various changes can be made therein without departing from the spirit and scope of the invention.

The invention claimed is:

1. A compound having the formula

R-A-D wherein,

R is a lipophilic moiety selected from the group consisting of:
(a) substituted and unsubstituted alkyl,
(b) substituted and unsubstituted branched alkyl,
(c) substituted and unsubstituted heteroalkyl,
(d) substituted and unsubstituted cycloalkyl,
(e) substituted and unsubstituted alkenyl,
(f) substituted and unsubstituted alkynyl,
(g) substituted and unsubstituted aryl, and
(h) substituted and unsubstituted aralkyl;

A is —C(=O)CH$_2$CH$_2$C(=O)—; and

D is an anticancer drug moiety, wherein the drug is camptothecin or a derivative thereof.

2. A compound of claim 1, wherein the anticancer drug moiety is 10-hydroxycamptothecin or a derivative thereof.

3. A compound of claim 1, wherein the anticancer drug moiety is 7-ethyl-10-hydroxycamptothecin or a derivative thereof.

4. A compound of claim 1, wherein the anticancer drug moiety is 9-aminocamptothecin or a derivative thereof.

5. A compound of claim 1, wherein the anticancer drug moiety is 9-amino-7-ethylcamptothecin or a derivative thereof.

6. A compound of claim 1, wherein the anticancer drug moiety is 10-aminocamptothecin or a derivative thereof.

7. A compound of claim 1, wherein the anticancer drug moiety is 10-amino-7-ethylcamptothecin or a derivative thereof.

8. A compound of claim 1 selected from the group consisting of:
(a) 10-(benzyl succinate)-7-ethylcamptothecin,
(b) 20-(benzyl succinate)camptothecin,
(c) 10-(4-methylbenzyl succinate)-7-ethylcamptothecin,
(d) 10-(2,4,6-trimethylbenzyl succinate)-7-ethylcamptothecin,
(e) 10-(2,3,4,5,6-pentamethylbenzyl succinate)-7-ethylcamptothecin,
(f) 10-(1-octyl succinate)-7-ethylcamptothecin, and
(g) 20-(1-octyl succinate)camptothecin.

9. A compound of claim 1, wherein R is benzyl.

10. A compound of claim 1, wherein R is n-alkyl.

11. An emulsion, comprising:
(a) an oil phase comprising
(i) compound of claim 1; and
(ii) a lipophilic medium; and
(b) an aqueous phase.

12. The emulsion of claim 11, wherein the lipophilic medium comprises a tocopherol.

13. A micelle formulation, comprising:
(a) compound of claim 1; and
(b) an aqueous phase.

14. A method for treating non-small cell lung cancer, breast cancer, colon cancer, or ovarian cancer, comprising administering to a subject in need thereof a therapeutically effective amount of a compound of claim 1.

15. The method of claim 14, wherein administering the compound comprises administering an emulsion comprising the compound.

16. The method of claim 14, wherein administering the compound comprises administering a micelle formulation comprising the compound.

* * * * *

UNITED STATES PATENT AND TRADEMARK OFFICE
CERTIFICATE OF CORRECTION

| | | Page 1 of 1 |
|---|---|---|
| PATENT NO. | : 7,786,134 B2 | |
| APPLICATION NO. | : 11/611457 | |
| DATED | : August 31, 2010 | |
| INVENTOR(S) | : Y. Zhang et al. | |

It is certified that error appears in the above-identified patent and that said Letters Patent is hereby corrected as shown below:

| COLUMN | LINE | ERROR |
|---|---|---|
| 30 (Claim 11, line 2) | 16 | "(i) compound" should read --(i) a compound-- |
| 30 (Claim 13, line 2) | 23 | "(a) compound" should read --(a) a compound-- |

Signed and Sealed this
Nineteenth Day of July, 2011

David J. Kappos
*Director of the United States Patent and Trademark Office*